United States Patent
Panayi et al.

(10) Patent No.: US 10,492,488 B2
(45) Date of Patent: Dec. 3, 2019

(54) EMULSIFIABLE CONCENTRATE COMPRISING A PHENOXY-ALKANOIC ACID HERBICIDE

(71) Applicant: NUFARM AUSTRALIA LIMITED, Laverton North, Victoria (AU)

(72) Inventors: Aristos Panayi, Taylors Hill (AU); Claudio Silva, Mitcham (AU); Chad Richard Ord Sayer, Brighton (AU); Sumit Sharma, Werribee (AU)

(73) Assignee: NUFARM AUSTRALIA LIMITED, Laverton North, Victoria (AU)

( * ) Notice: Subject to any disclaimer, the term of this patent is extended or adjusted under 35 U.S.C. 154(b) by 0 days.

(21) Appl. No.: 15/571,760

(22) PCT Filed: May 6, 2016

(86) PCT No.: PCT/AU2016/050336
§ 371 (c)(1),
(2) Date: Nov. 3, 2017

(87) PCT Pub. No.: WO2016/176742
PCT Pub. Date: Nov. 10, 2016

(65) Prior Publication Data
US 2018/0139955 A1 May 24, 2018

(30) Foreign Application Priority Data

May 7, 2015 (AU) .............................. 2015901641

(51) Int. Cl.
*A01N 25/02* (2006.01)
*A01N 25/04* (2006.01)
*A01N 39/04* (2006.01)

(52) U.S. Cl.
CPC ............. *A01N 25/02* (2013.01); *A01N 25/04* (2013.01); *A01N 39/04* (2013.01)

(58) Field of Classification Search
None
See application file for complete search history.

(56) References Cited

U.S. PATENT DOCUMENTS

| 4,213,776 | A | 7/1980 | Giilck et al. |
| 8,044,059 | B2 | 10/2011 | Hopkins et al. |
| 8,426,341 | B2 | 4/2013 | Volgas et al. |
| 2002/0107149 | A1 | 8/2002 | Volgas et al. |
| 2003/0211943 | A1 | 11/2003 | Harwell |
| 2009/0062121 | A1 | 3/2009 | Satchivi et al. |
| 2009/0215797 | A1 | 8/2009 | Hopkins et al. |
| 2010/0016163 | A1 | 1/2010 | Keiper et al. |
| 2010/0105558 | A1 | 4/2010 | Li et al. |
| 2014/0371075 | A1 | 12/2014 | Dieleman et al. |
| 2015/0105254 | A1 | 4/2015 | Li |
| 2016/0050919 | A1 | 2/2016 | Byrne et al. |
| 2018/0139955 | A1 | 5/2018 | Panayi et al. |
| 2018/0153160 | A1 | 6/2018 | Chetty et al. |

FOREIGN PATENT DOCUMENTS

| EP | 2815649 | A1 | 12/2014 |
| GB | 1079622 | A | 8/1967 |
| WO | 2007/030885 | A1 | 3/2007 |
| WO | 2007/140332 | A2 | 12/2007 |
| WO | 2011/019652 | A2 | 2/2011 |
| WO | 2011/080208 | A1 | 7/2011 |
| WO | 2011/082162 | A1 | 7/2011 |
| WO | 2012/003441 | A1 | 1/2012 |
| WO | 2012/040785 | A1 | 4/2012 |
| WO | 2013/082016 | A1 | 6/2013 |
| WO | 2013/126947 | A1 | 9/2013 |
| WO | 2015/054561 | A1 | 4/2015 |
| WO | 2016/050782 | A1 | 4/2016 |

OTHER PUBLICATIONS

International Search Report and Written Opinion for corresponding Application No. PCT/AU2016/050336 (dated Jun. 10, 2016).
International Preliminary Report on Patentability for corresponding Application No. PCT/AU2016/050336 (dated Sep. 4, 2017).
Extended European Search Report for Application No. 16788966.6 (dated Oct. 19, 2018).
International Search Report and Written Opinion for Application No. PCT/AU2016/050334 (dated Jul. 4, 2016).
International Preliminary Report on Patentability for Application No. PCT/AU2016/050334 (dated Mar. 28, 2017).
Anon, "Material Safety Data Sheet: Product Name: Solvesso 200 Fluid," Pure Chemicals Co., Chennai, Tamilnadu, India (2014).
International Search Report and Written Opinion for Application No. PCT/AU2016/050337 (dated Jun. 7, 2016).
Extended European Search Report for Application No. 16788968 (dated Nov. 2, 2018).
Armel et al., "Common Commercial Pre-Packaged Herbicide Mixtures," UT Extension 1-28 (2008).

*Primary Examiner* — Alton N Pryor
(74) *Attorney, Agent, or Firm* — Pepper Hamilton LLP

(57) ABSTRACT

An emulsifiable concentrate of a phenoxy-alkanoic acid herbicide comprising a phenoxy-alkanoic acid herbicide dissolved in an amide solvent and at least one amine.

21 Claims, No Drawings

EMULSIFIABLE CONCENTRATE COMPRISING A PHENOXY-ALKANOIC ACID HERBICIDE

This application is a national stage application under 35 U.S.C. § 371 of PCT Application No. PCT/AU2016/050336, filed May 6, 2016, which claims the priority benefit of Australia Patent Application No. 2015901641, filed May 7, 2015.

FIELD

The invention relates to an emulsifiable concentrate composition comprising a phenoxy-alkanoic acid herbicide a process for preparation of the composition and method for control of plant growth using the composition.

BACKGROUND

Auxin herbicides have proven to be effective for control of unwanted plants. Phenoxy-alkanoic acid herbicides include 2,4-D (2,4-dichlorophenoxyacetic acid), 2,4-DB (4-(2,4-dichlorophenoxy)butanoic acid), dichloroprop (2-(2,4-dichlorophenoxy)propanoic acid), dicloprop-P, MCPA ((4-chloro-2-methylphenoxy)acetic acid), MCPB (4-(4-chloro-2-methylphenoxy)butanoic acid), mecoprop (2-(4-chloro-2-methylphenoxy)propanoic acid) and mecoprop-P.

Phenoxy-alkanoic acid herbicides in the acid form have poor solubility in water and are commonly formulated as an ester, such as the methyl ester or an amine salt such as the dimethylamine salt. The Phenoxy-alkanoic esters, such as the methyl ester, are more active than the salts but are more likely to volatilize with the potential to damage off-target plants. The Phenoxy-alkanoic esters and auxin amine salts are each converted in the target plants to the acid which is active in controlling plant growth. It is desirable to formulate the acids as a stable concentrate.

Some acid herbicides from the auxin class have been formulated in the form of the acid. Volgas et al. (U.S. Pat. No. 8,426,341) discloses an acid herbicide concentrate with a specific alcohol ethoxylate surfactant which forms a microemulsion on dilution with water.

Groenewegen et al. (US 2012/0283103) describes the use of certain fatty acid amide solvents to form concentrate emulsions (CEs) and emulsifiable concentrates (ECs) of auxin herbicides. The amide solvents are said to have high solvency for water insoluble compounds in preparing concentrates in the form of an emulsion (CEs) and emulsifiable concentrates (ECs).

Concentrated emulsions (CEs) contain water which necessarily reduces the potential loading of the active. We have found that emulsifiable concentrates of Phenoxy-alkanoic acids still have poor solution stability even in amide solvents and on cold storage give rise to crystal formation in the concentrate and/or crystal formation on dilution of the concentrate to form an emulsion. Poor storage stability and the consequential formation of precipitates can disrupt effective use of the herbicide through clogging of spray equipment and/or dosing of the herbicide at a lower rate than desired.

There is a need for a more highly stable emulsifiable concentrate of phenoxy-alkanoic acid herbicides.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

We provide an emulsifiable concentrate of a phenoxy-alkanoic acid herbicide comprising a phenoxy-alkanoic acid herbicide dissolved in an amide solvent and at least one amine.

The amine (which when there is more than one said amine is the total of the amines) is preferably present in an amount of from 0.5% to 5% by weight more preferably from 2% to 5%, still more preferably from 3% to 5% by weight of the amine based on the weight of the emulsifiable concentrate.

There is further provided a method for the preparation of an emulsifiable concentrate of phenoxy-alkanoic acid herbicide comprising combining said phenoxy-alkanoic acid herbicide with an amide solvent and at least one amine (preferably in an amount of from 0.5% to 5% by weight, more preferably from 2% to 5%, still more preferably from 3% to 5% by weight of a tri-alkanolamine based on the weight of the emulsifiable concentrate) and heating the compositions, preferably to a temperature of at least 40° C., more preferably 50° C., still more preferably at least 60° C. and most preferably at least 65° C., to provide a solution of the phenoxy-alkanoic acid herbicide.

There is further provided a method of controlling weeds comprising providing a phenoxy-alkanoic acid emulsifiable concentrate according to the above, diluting the concentrate with water to provide an emulsion and applying the diluted concentrate to the weeds to be controlled.

We have further found that the emulsifiable concentrate may result in formation of a minor proportion of esters and amides of the phenoxyalkanoic acids on storage. While the esters and amides may be active herbicides, in order to avoid in situ formation of esters and/or amides it is particularly preferred to include a small amount of water, preferably from 0.5 to 5% by weight water based on the weight of the emulsifiable concentrate more preferably from 0.5% to 3%, still more preferably from 1% to 3%, by weight water based on the weight of the emulsifiable concentrate

DETAILED DESCRIPTION

The term "emulsion", as used herein, refers to a fine dispersion of minute droplets of one liquid in another in which it is not soluble or miscible and includes microemulsions and macroemulsions. The term "emulsifiable concentrates" refers to concentrates which, on dilution, form either microemulsions or macroemulsions.

Throughout the description and the claims of this specification the word "comprise" and variations of the word, such as "comprising" and "comprises" is not intended to exclude other additives, components, integers or steps.

The reference to a phenoxy-acid herbicide herein, except where the context determines otherwise, refers to the phenoxy-alkanoic acid herbicide in the form of the free acid.

The concentrate composition comprises a phenoxy-alkanoic acid herbicide. Typically said phenoxy-alkanoic acid herbicide will be present in a total amount of at least 200 g acid per litre of emulsifiable concentrate preferably at least 250 g/L, more preferably at least 300 g/L, still more preferably at least 350 g/L and most preferably at least 380 g/L phenoxy-alkanoic acid herbicide. In some embodiments the concentration of phenoxy acid herbicide is at least 400 g/L such as at least 450 g/L or at least 500 g/L of the emulsifiable concentrate. The phenoxy-alkanoic acid herbicide may consist of a single herbicide or mixture of two or more phenoxy-alkanoic acid herbicides.

The preferred phenoxy-alkanoic acid herbicide includes at least one selected from the group consisting of:
phenoxyacetic herbicides including 2,4-D and MCPA;
phenoxybutyric herbicides including 4-CPB, 2,4-DB, 3,4-DB, MCPB and 2,4,5-TB; and
phenoxypropionic herbicides including dichlorprop, dichlorprop-P, fenoprop, mecoprop and mecoprop-P.

The more preferred herbicides are selected from the group consisting of 2,4-D, MCPA, diclorop, dicloprop-P, mecoprop and mecoprop-P. In a particularly preferred set of embodiments the emulsifiable concentrate comprises 2,4-D in an amount of at least 200 g acid per litre of emulsifiable concentrate preferably at least 250 g/L, more preferably at least 300 g/L, still more preferably at least 350 g/L and most preferably at least 380 g/L.

The emulsifiable concentrate composition comprises an amine. The amine is typically a primary secondary or tertiary amine and may comprise aliphatic straight or branched chain substituents, aliphatic ring substituents or may comprise the heteroatom of a aliphatic hetercyclic amine. The amine may comprise a plurality of amine groups and/or mixture of amines.

In one embodiment the amine comprises at least one amine of formula (I)

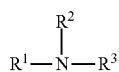

(I)

wherein $R^1$, $R^2$ and $R^3$ are independently selected from the group consisting of hydrogen, $C_1$ to $C_{10}$ alkyl; $C_5$ or $C_6$ cycloaliphatic optionally substituted with from one to four $C_1$ to $C_4$ alkyl groups and/or an amino-$C_1$ to $C_4$ alkyl group; $C_1$ to $C_{10}$ alkyl substituted with a substituent selected from the group consisting of hydroxyl, $C_1$ to $C_{10}$ alkoxy, amino, ($C_1$ to $C_6$ alkyl)amino and di-($C_1$ to $C_6$ alkyl)amino; and the group wherein two of $R^1$, $R^2$ and $R^3$ together form a ring of 5 or 6 constituent ring members selected from methylene, —O—, —N— and —N($C_1$ to $C_6$-alkyl)- and the other of $R^1$, $R^2$ and $R^3$ is selected from hydrogen, $C_1$ to $C_6$ alkyl and $C_1$ to $C_6$ alkyl substituted with a substituent selected from the group consisting of hydroxyl, $C_1$ to $C_6$ alkoxy, amino and ($C_1$ to $C_6$ alkyl)amino; and wherein at least one of $R^1$, $R^2$ and $R^3$ is other than hydrogen.

In one set of embodiments the amine is of formula I wherein $R^1$, $R^2$ and $R^3$ are independently selected from the group selected from hydrogen and $C_1$ to $C_{10}$ alkyl wherein at least one of $R^1$, $R^2$ and $R^3$ is $C_1$ to $C_{10}$ alkyl. Preferred amines in this group are mono-, di- and tri-($C_1$ to $C_6$ alkyl)amines and preferably tri-($C_1$ to $C_4$ alkyl)amines such as triethylamine.

In a further set of amines of formula I $R^1$, $R^2$ and $R^3$ are independently selected from the group consisting of hydrogen, $C_1$ to $C_{10}$ alkyl and $C_1$ to $C_{10}$ alkyl substituted with a substituent selected from the group consisting of hydroxyl, $C_1$ to $C_{10}$ alkoxy, amino, ($C_1$ to $C_6$ alkyl)amino and di-($C_1$ to $C_6$ alkyl)amino wherein at least one of $R^1$, $R^2$ and $R^3$ is other than hydrogen and $C_1$ to $C_{10}$ alkyl. Examples of amines in this group include compounds of formula I wherein $R^1$, $R^2$ and $R^3$ are independently selected from hydrogen, $C_1$ to $C_6$ alkyl and $C_1$ to $C_6$ alkyl substituted with a substituent selected from the group consisting of hydroxyl, $C_1$ to $C_6$ alkoxy, amino, ($C_1$ to $C_4$ alkyl)amino and di-($C_1$ to $C_4$ alkyl)amino wherein at least one of $R^1$, $R^2$ and $R^3$ is other than hydrogen and $C_1$ to $C_6$ alkyl. More specific examples of compounds include ($C_1$ to $C_6$ alkanol)amines, di-($C_1$ to $C_6$ alkanol)amines, tri-($C_1$ to $C_6$ alkanol)amines di-($C_1$ to $C_6$ alkyl) ($C_1$ to $C_6$ alkanol)amines, (amino $C_1$ to $C_6$ alkyl)di-($C_1$ to $C_6$ alkyl)amines, di(-amino-$C_1$ to $C_6$ alkyl) alkylamines.

In a further set of amines of Formula I two of $R^1$, $R^2$ and $R^3$ together form a ring, incorporating the amine nitrogen, of 5 or 6 constituent ring members selected from the group consisting of methylene and optionally a further heteroatom ring member selected from —O—, —N(H)— and —N($C_1$ to $C_6$-alkyl)-; and the other of $R^1$, $R^2$ and $R^3$ is selected from hydrogen, $C_1$ to $C_6$ alkyl and $C_1$ to $C_6$ alkyl substituted with a substituent selected from the group consisting of hydroxyl, $C_1$ to $C_6$ alkoxy, amino and ($C_1$ to $C_6$ alkyl)amino The constituent ring members where at least two of $R^1$, $R^2$ and $R^3$ form a heterocyclic ring of 5 or 6 constituent members may, for example, be a ring selected from the group consisting of pyrrolidine, piperidine, morpholine and piperazine.

The preferred amines are of formula I

(I)

wherein either (i) $R^1$, $R^2$ and $R^3$ are $C_2$ to $C_4$ alkanol or (ii) $R^1$ is $C_1$ to $C_{10}$ alkoxy substituted $C_2$ to $C_4$ alkyl and $R^2$ and $R^3$ are independently hydrogen or $C_1$ to $C_4$ alkyl.

More preferably the amines are trialkanolamines and alkoxyamines are of formula (I) wherein (i) $R^1$, $R^2$ and $R^3$ are independently selected from $C_2$ to $C_4$ alkanol (more preferably triethanolamine and triisopropanolamine) or (ii) $R^1$ is selected from $C_1$ to $C_6$ alkoxy-substituted alkyl and $R^2$ and $R^3$ are hydrogen or $C_1$ to $C_4$ alkyl such as methyl (preferably $R^2$ and $R^3$ hydrogen).

Specific examples of amines selected from trialkanolamines, alkoxyalkylamines and mixtures thereof include triethanolamine, tripropanolamine, methoxypropylamine and hexyloxypropylamine.

The trialkanolamine is preferably selected from the group consisting of tri-($C_2$ to $C_4$ alkanol)amines such as triethanolamine, triisopropanolamine and mixtures thereof.

The amine is preferably present in an amount of from 0.5% to 5% by weight more preferably 1% to 5% by weight, still more preferably 2% to 5% by weight, still more preferably from 3% to 5% by weight and most preferably from 4% to 5% by weight of the amine based on the weight of the emulsifiable concentrate.

The emulsifiable concentrate composition comprises an amide solvent. The amide solvent is, in one set of embodiments, present in an amount of from 25% to 60% by weight of the composition, preferably from 25% to 50% and more preferably from 25% to 45% by weight of the emulsifiable concentrate composition.

Examples of suitable amide solvents include compounds of formula II:

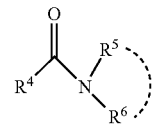

II wherein $R^4$ is selected from the group consisting of hydrogen and $C_1$ to $C_{17}$ hydrocarbyl;

$R^5$ is selected from the group consisting of $C_1$ to $C_{15}$ hydrocarbyl;

$R^6$ is selected from the group consisting of $C_1$ to $C_{15}$ hydrocarbyl; and $R^5$ and $R^6$ may together from a ring incorporating the nitrogen of the amide comprising 4 or 5 methylene groups; preferred examples of $R^5$ and $R^6$ are independently selected from the group consisting of $C_1$ to $C_6$ hydrocarbyl and the group wherein $R^5$ and $R^6$ together form a ring incorporating the nitrogen of the amine by a bridging group $R^5 \ldots R^6$ of formula —$CH_2\,CH_2\,CH_2\,CH_2$— or —$CH_2\,CH_2\,CH_2\,CH_2\,CH_2$—.

In one embodiment the amide solvent is of formula II wherein $R^4$ is selected from the group consisting of $C_3$ to $C_{17}$ alkyl, preferably $C_6$ to $C_{17}$ aliphatic; and $R^5$ and $R^6$ are independently selected from the group $C_1$ to $C_6$ alkyl and the group wherein $R^5$ and $R^6$ together form a bridging group of formula selected from the group consisting of —$CH_2\,CH_2\,CH_2\,CH_2$— and —$CH_2\,CH_2\,CH_2\,CH_2\,CH_2$—, preferably $R^5$ and $R^6$ are independently selected from $C_1$ to $C_4$ alkyl or the group wherein $R^5$ and $R^6$ together form a bridging group of formula —$CH_2\,CH_2\,OCH_2\,CH_2$—, —$CH_2\,CH_2\,CH_2\,CH_2$— and —$CH_2\,CH_2\,CH_2\,CH_2\,CH_2$—.

In a preferred set of embodiments, the amide solvent of formula II wherein $R^4$ is $C_6$ to $C_{17}$ alkyl; and $R^5$ and $R^6$ are independently selected from $C_1$ to $C_4$ alkyl such as methyl, ethyl, n-propyl, isopropyl.

Examples of the amide solvents include N,N-dimethyl fatty acid amides such as N,N-dimethyl $C_8$ to $C_{16}$ fatty acid amide.

The preferred amide "solvents" are fatty acid amides comprising a $C_5$ to $C_{17}$ aliphatic group.

Specific examples of amide solvents include:

N,N-dimethyl-octanamide, N,N-dimethyl-decanamide,
N,N-dimethyl-caprylamide, N,N-dimethyl-2-ethyl-hexanoamide,
N,N-dimethyl-oleamide N,N-dimethyl-lauricamide (also known as N,N-dimethyldodecanamide), N,N-dimethyl-myristicamide (also known as N,N-dimethyltetradecanamide), N,N-dimethyl-9-decenamide and mixtures of two or more thereof.

The emulsifiable concentrate may and preferably will, include a hydrocarbon co-solvent. The hydrocarbon co-solvent preferably has a flash point of at least 60.5° C. The hydrocarbon co-solvent preferably comprises at least one hydrocarbon selected from alkyl substituted aromatics such as mono-, di- and trialkyl benzenes and alkyl naphthalenes. For example, $C_9$ alkyl benzene is reported to have a flash point of 42° C. whereas $C_{10}$ alkylbenzene is reported to have a flash point of 66° C. A preferred co-solvent is a mixture of $C_8$ to $C_{12}$ di- and tri-alkyl benzenes, commercially available from Exxon Mobil as Solvesso 150™ and Solvesso 200™.

The hydrocarbon co-solvent is preferably in the range of from 2% to 25% w/w of the emulsifiable concentrate. Preferably the hydrocarbon co-solvent is present in an amount of from 5% to 20% w/w and more preferably from 5% to 15% w/w of the emulsifiable concentrate.

The emulsifiable concentrate will typically comprise an emulsifier component. The emulsifier component may, for example, comprise from 2% w/w to 25% w/w of the emulsifiable concentrate. The emulsifier component preferably comprises from 5% w/w to 20% w/w and more preferably from 5% w/w to 15% w/w of the concentrate composition.

The emulsifier component may include anionic, non-ionic, cationic or mixed types of emulsifiers. In one embodiment the concentrate comprises an anionic emulsifier (preferably an alkylarylsulfonate) in an amount in the range of from 1% w/w to 10% w/w of the concentrate.

The emulsifiable concentrate preferably comprises an alkylarylsulfonate anionic emulsifier. Alkylarylsulfonates are anionic surfactants and are available in compositions containing suitable counterions which may be optionally substituted ammonium and metal counterions. Examples of alkylarylsulfonates include butylnaphthalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid. Benzenesulfonates, such as alkyl- or arylbenzenesulfonates, e.g. (poly)alkyl- and (poly)arylbenzenesulfonates which are acidic and neutralized with suitable bases, for example having 1 to 12 carbon atoms per alkyl radical or having up to 3 styrene units in the polyaryl radical, preferably (linear) dodecylbenzenesulfonic acid and oil-soluble salts thereof, such as, for example, the calcium salt or the isopropylammonium salt of dodecylbenzenesulfonic acid.

It is particularly preferred that the composition of the invention contain a salt of dodeclybenzenesulfonic acid and most preferably calcium dodecylbenzenesulfonate.

The emulsifiable concentrate preferably comprises a non-ionic surfactant component. Preferred non-ionic surfactants include the condensation products of alkylene oxide with components forming nonpolar groups such as the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal.

Examples of nonionic surfactants which may be used alone or in combination in the emulsifier component are listed below, in which EO=ethylene oxide units, such as PO=propylene oxide units and BO=butylene oxide units:

$C_{10}$-$C_{24}$-alcohols which may be alkoxylated, e.g. with 1-60 alkylene oxide units, preferably 1-60 EO and/or 1-30 PO and/or 1-15 BO in any order. The terminal hydroxyl groups of these compounds can be terminally capped by an alkyl, cycloalkyl or acyl radical having 1-24 carbon atoms. Examples of such compounds are: Genapol® C, L, O, T, UD, UDD, X products from Clariant, Plurafac® and Lutensol® A, AT, ON, TO products from BASF, Marlipal® 24 and O13 products from Condea, Dehypon® products from Henkel, Ethylan® products from Akzo Nobel, such as Ethylan CD 120.

Copolymers consisting of EO, PO and/or BO units, such as, for example, block copolymers, such as the Pluronic® products from BASF and the Synperonic® products from Uniquema with a molecular weight of from 400 to $10^8$.

Alkyleneoxy adducts of $C_1$-$C_9$ alcohols, such as Atlox® 5000 from Uniquema or Hoe®-S3510 from Clariant.

Fatty acid and triglyceride alkoxylates, such as the Serdox® NOG products from Condea or alkoxylated plant oils, such as soybean oil, rapeseed oil, corn oil, sunflower oil, cottonseed oil, linseed oil, coconut oil, palm oil, thistle oil, walnut oil, peanut oil, olive oil or rhicinus oil (i.e. castor oil), in particular rapeseed oil and castor oil, plant oils also being understood as meaning their transesterification products, e.g. alkyl esters, such as rapeseed oil methyl ester or rapeseed oil ethyl ester, for example the Emulsogen® products from Clariant, salts of aliphatic, cycloaliphatic and olefinic carboxylic acids and polycarboxylic acids, and alpha-sulfo fatty acid esters as available from Henkel. Particularly preferred in this group are castor oil ethoxylates such as TERMUL® ®1284 and TERMUL® ®1285 from Huntsman.

Fatty acid amide alkoxylates, such as the Comperlan® products from Henkel or the Amam® products from Rhodia.

Alkyleneoxy adducts of alkynediols, such as the Surfynol® products from Air Products. Sugar derivatives, such as amino and amido sugars from Clariant, glucitols from Clariant, alkyl polyglycosides in the form of the APG® products from Henkel or such as sorbitan esters in the form of the Span® or Tween® products from Uniquema or cyclodextrine esters or ethers from Wacker.

Alkyleneoxy adducts based on polyol, such as Polyglycol® products from Clariant. Interface-active polyglycerides and derivatives thereof from Clariant. Surface-active compounds based on silicone and/or silane, such as the Tegopren® products from Goldschmidt and the SE® products from Wacker, and the Bevaloid®, Rhodorsil® and Silcolapse® products from Rhodia (Dow Corning, Reliance, GE, Bayer).

Per- or polyfluorinated surface-active compounds, such as Fluowet® products from Clariant, the Bayowet® products from Bayer, the Zonyl® products from Du Pont and products of this type from Daikin and Asahi Glass.

Interface-active sulfonamides, e.g. from Bayer.

Surface-active polyvinyl compounds, such as modified polyvinylpyrolidone, such as the Luviskol® products from BASF and the Agrimer® products from ISP or the derivatized polyvinylacetates, such as the Mowilith® products from Clariant or the butyrates, such as the Lutonal® products from BASF, the Vinnapas® and the Pioloform® products from Wacker or modified polyvinyl alcohols, such as the Mowiol® products from Clariant.

Surface-active polymers based on maleic anhydride and/or reaction products of maleic anhydride, and maleic anhydride and/or reaction products of copolymers which include maleic anhydride, such as the Agrimer®-VEM A products from ISP.

Surface-active derivatives of montane, polyethylene and polypropylene waxes, such as the Hoechst® waxes or the Licowet® products from Clariant.

Poly- or perhalogenated surfactants, such as, for example Emulsogen®-1557 from Clariant.

Phenols which may be alkoxylated, for example phenyl ($C_1$-$C_4$)alkyl ethers or (poly)alkoxylated phenols [=phenol (poly)alkylene glycol ethers], for example having 1 to 50 alkyleneoxy units in the (poly)alkyleneoxy moiety, where the alkylene moiety preferably in each case has 1 to 4 carbon atoms, preferably phenol reacted with 3 to 10 mol of alkylene oxide.

(poly)alkylphenols or (poly)alkylphenol alkoxylates [polyalkylphenol (poly)alkylene glycol ethers], for example with 1 to 12 carbon atoms per alkyl radical and 1 to 150 alkyleneoxy units in the polyalkyleneoxy moiety, preferably tri-n-butylphenol or triisobutylphenol reacted with 1 to 50 mol of ethylene oxide, polyarylphenols or polyarylphenol alkoxylates [=polyarylphenol (poly)alkylene glycol ethers], for example tristyrylphenol polyalkylene glycol ethers with 1 to 150 alkyleneoxy units in the polyalkyleneoxy moiety, preferably tristyrylphenol reacted with 1 to 50 mol of ethylene oxide.

Examples of surfactants from the group of aromatic-based surfactants are the surfactants of the abovementioned groups, preferably phenol reacted with 4 to 10 mol of ethylene oxide, available commercially, for example, in the form of the Agrisol® products (Akcros), triisobutylphenol reacted with 4 to 50 mol of ethylene oxide, commercially available, for example, in the form of the Sapogenat® T products (Clariant), nonylphenol reacted with 4 to 50 mol of ethylene oxide, commercially available, for example, in the form of the Arkopal® products (Clariant), tristyrylphenol reacted with 4 to 150 mol of ethylene oxide, for example from the Soprophor® series, such as Soprophor® FL, Soprophor® 3D33, Soprophor® BSU, Soprophor® 4D-384, Soprophor® CY/8 (Rhodia).

The non-ionic emulsifier present in the compositions of the invention may comprise one such surfactant or a blend of two or more non-ionic surfactants.

The emulsifier is more preferably selected from alcohol ethoxylates, fatty acid ethoxylates, fatty amide ethoxylates and EO/PO block copolymers including butyl based block copolymers. The non-ionic emulsifier preferably comprises in the range of from 2% w/w to 25% w/w of the composition. More preferably the non-ionic emulsifier comprises in the range of from 2% w/w to 20% w/w and more preferably from 2% w/w to 15% w/w of the concentrate.

In one embodiment, the anionic emulsifier (preferably an alkylaryl sulfonate) comprises from 1% to 10% w/w of the composition and the non-ionic emulsifier comprises from 2% to 15% w/w of the composition.

We have found that over a period of time the phenoxyalkanoic acid concentration in the emulsifiable concentrate is reduced by formation of ester and/or amide derivatives of the phenoxy acid. This problem has not previously been recognised but is believed to occur in the presence of amines. The problem regarding loss of active ingredients in acid emulsifiable concentrate (EC) formulations was discovered during the development of the phenoxy-alkanoic acid emulsifiable concentrate compositions, particularly 2,4-D acid EC formulations. Samples of 2,4-D acid EC formulations were initially tested for 2,4-content via a HPLC method specific to free 2,4-D acid. During formulation development and after subjecting formulations to a 2 weeks at 54° C. accelerated stability study a decreased level of 2,4-D free acid was found when compared to initial sample assay results. A method which was developed and validated for assaying total 2,4-D content via hydrolysis provided evidence that the loss in free acid content was via the speciation of 2,4-D acid into unknown transformation products. Subsequent work to identify the 2,4-D species was carried out via LCMS (Liquid chromatography with positive electrospray ionization and time of flight mass spectrometry detection). The LCMS technique was successful in the identification and characterisation of a number of 2,4-D transformation species. This methodology was further utilsed in the identification of transformation products in MCPA acid EC formulations.

The transformation products were found to be esters and/or amides derived from the phenoxy-alkanoic acid herbicide in the presence of the amine. We have found that under the conditions found in EC formulations the carboxylic acid moiety present in the active ingredients; 2,4-D, MCPA react with base ingredients containing primary and secondary amine groups to produce amides and with alcohol groups to produce esters as shown, for example, in Schemes 1 and 2 relating to 2,4-D. Note not all possible reaction schemes are provided below, as numerous iterations of alkyl, alkoxyl and ethanolamine type bases where tested during the formulation development stage.

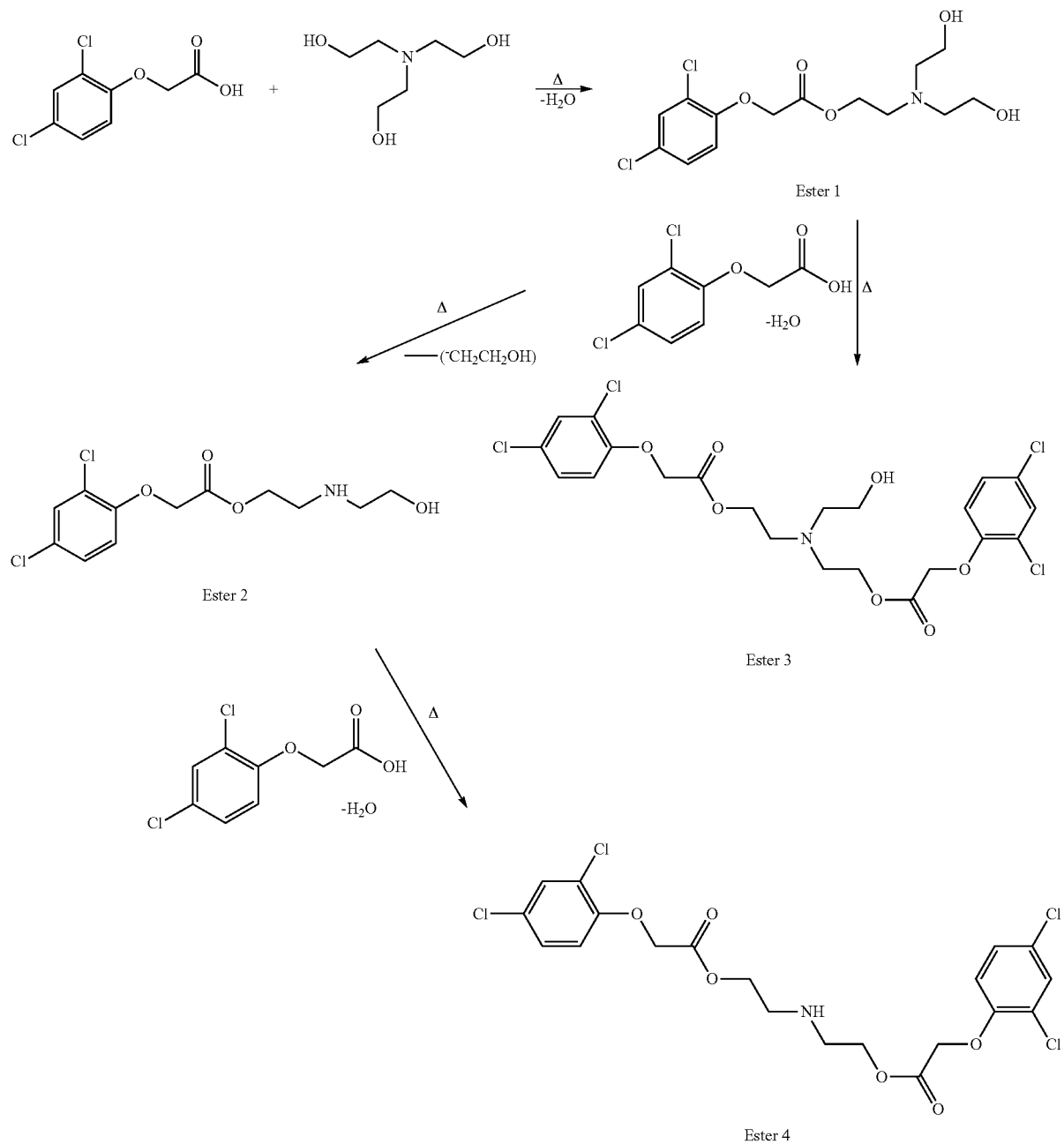

Reaction Scheme 2-Reaction of 2,4-D with methoxypropylamine (MOPA)

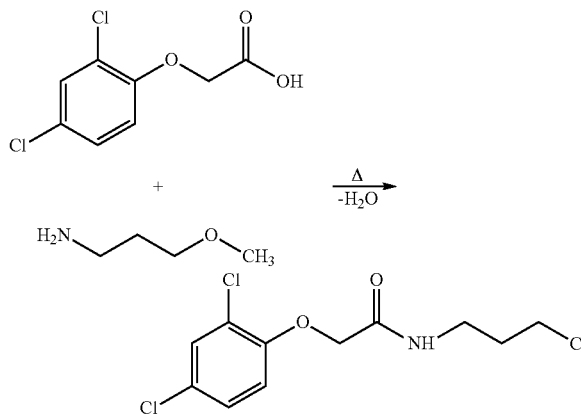

The reactions of carboxylic acids with amines are generally considered to proceed via an activation of the carboxylic acid prior to amide formation. It is unclear how these reactions are catalyzed/activated in the EC formulations, however addition of water reduces significantly the formation of these transformed phenoxyalkanoic acid herbicides.

The esters and amides retain a level of herbicidal activity but it is desirable to retain the phenoxy-alkanoic acid as a stable long term active.

We have found that the addition of small amounts of water maintains the active ingredients predominantly in their acid form. The amount of water can be determined for any composition bearing in mind the desire to avoid formation of ester and amide derivatives.

Generally speaking the amount of water is at least 0.5% by weight water based on the weight of the emulsifiable concentrate. More preferably the water is present in an amount of from 0.5% to 3%, still more preferably from 1% to 3% by weight water based on the weight of the emulsifiable concentrate.

In one set of embodiments the concentrate composition comprises:

Phenoxy-alkanoic acid herbicide selected from the group consisting of 2,4-D, MCPA, diclorop, dicloprop-P, mecoprop, mecoprop-P, clopyralid and triclopyr (most preferably 2,4-D) in an amount of at least 250 g/L, more preferably at least 300 g/L and still more preferably at least 350 g/L, even more preferably at least 380 g/L (such as in some embodiments where the concentration of phenoxy acid herbicide is at least 400 g/L, at least 450 g/L or at least 500 g/L of the emulsifiable concentrate); amide solvent, preferably fatty acid amide in an amount of from 25% to 60% w/w of the composition, more preferably 25% to 50% w/w and most preferably 25% to 45% w/w of the concentrate;

hydrocarbon co-solvent preferably selected from the group of $C_8$-$C_{12}$ di- and tri-alkylbenzenes in an amount of from 2% to 25% w/w, more preferably 5% to 20% w/w and most preferably 5% to 15% w/w of the concentrate;

anionic emulsifier in an amount of from 1% to 10% w/w of the composition;

non-ionic emulsifier in an amount of from 2% to 25% w/w, more preferably 2% to 20% w/w and still more preferably 2% to 15% w/w of the concentrate composition; and trialkanolamine (preferably selected from triethanolamine, triisopropanolamine and mixtures thereof), alkoxyalkylamine (preferably selected from methoxyalkylamine) and mixtures of two or more thereof, in an amount of from 0.5% to 20% w/w of the concentrate, more preferably from 3% to 15% w/w of the concentrate and still more preferably from 5% to 15% w/w based on the total weight of said phenoxy-alkanoic acid auxin herbicides.

The composition preferably contains water in an amount of at least 0.5% by weight water based on the weight of the emulsifiable concentrate. More preferably the water is present in an amount of from 0.5% to 3%, still more preferably from 1% to 3% by weight water The composition of the invention has been found to provide good storage stability and also forms an emulsion on dilution with water which has good stability to allow effective application to plants.

There is further provided a method for the preparation of an emulsifiable concentrate of auxin acid selected from the group consisting of phenoxy acid auxin herbicides and pyridine auxin herbicides and mixtures thereof (preferably the auxin acid herbicides are selected from the group consisting of 2,4-D, MCPA, diclorop, dicloprop-P, mecoprop, mecoprop-P, clopyralid and triclopyr and most preferably 2,4-D) comprising combining said phenoxy-alkanoic acid with an amide solvent and amine and heating the compositions, preferably to a temperature of at least 40° C., more preferably 50° C., still more preferably at least 60° C. and most preferably at least 65° C., to provide a solution of the auxin acid.

In a further aspect, the invention provides a method of controlling weeds comprising providing an emulsifiable concentrate as hereinbefore described; diluting the concentrate with water to form an emulsion and applying the diluted composition to the weeds.

The composition may comprise one or more further actives selected from the group consisting of herbicides fungicides, insecticides, plant growth regulators and biologicals.

Examples of additional herbicides may be selected from the following classes:
amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam;
anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil;
arylalanine herbicides such as benzoylprop, flamprop and flamprop-M;
chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor;
sulfonanilide herbicides such as benzofluor, cloransulam, diclosulam, florasulam, flumetsulam, metosulam, perfluidone, pyrimisulfan and profluazol;
sulfonamide herbicides such as asulam, carbasulam, fenasulam, oryzalin, penoxsulam and pyroxsulam, see also sulfonylurea herbicides;
thioamide herbicides such as bencarbazone and chlorthiamid;
antibiotic herbicides such as bilanafos;
benzoic acid herbicides such as dicamba, chloramben, 2,3,6-TBA and tricamba;

pyrimidinyloxybenzoic acid herbicides such as bispyribac and pyriminobac;
pyrimidinylthiobenzoic acid herbicides such as pyrithiobac;
phthalic acid herbicides such as chlorthal;
quinolinecarboxylic acid herbicides such as quinclorac and quinmerac;
arsenical herbicides such as cacodylic acid, CMA, DSMA, hexaflurate, MAA, MAMA, MSMA, potassium arsenite and sodium arsenite;
benzoylcyclohexanedione herbicides such as mesotrione, sulcotrione, tefuryltrione and tembotrione;
benzofuranyl alkylsulfonate herbicides such as benfuresate and ethofumesate;
carbamate herbicides such as asulam, carboxazole, chlorprocarb, dichlormate, fenasulam, karbutilate and terbucarb;
carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep;
cyclohexene oxime herbicides such as alloxydim, butroxydim, clethodim, cloproxydim, cycloxydim, profoxydim, sethoxydim, tepraloxydim and tralkoxydim;
cyclopropylisoxazole herbicides such as isoxachlortole and isoxaflutole;
dicarboximide herbicides such as benzfendizone, cinidon-ethyl, flumezin, flumiclorac, flumioxazin, and flumipropyn;
dinitrophenol herbicides such as dinofenate, dinoprop, dinosam, dinoseb, dinoterb, DNOC, etinofen and medinoterb;
diphenyl ether herbicides such as ethoxyfen;
nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen;
dithiocarbamate herbicides such as dazomet and metam;
halogenated aliphatic herbicides such as alorac, chloropon, dalapon, flupropanate, hexachloroacetone, iodomethane, methyl bromide, monochloroacetic acid, SMA and TCA;
imidazolinone herbicides such as imazamethabenz, imazamox, imazapic, imazapyr, imazaquin and imazethapyr;
nitrile herbicides such as bromobonil, bromoxynil, chloroxynilm, iodobonil, ioxynil and pyraclonil;
organophosphorus herbicides such as amiprofos-methyl, anilofos, bensulide, bilanafos, butamifos, 2,4-DEP, DMPA, EBEP, fosamine, glufosinate, glyphosate, and piperophos;
oxadiazolone herbicides such as dimefuron, methazole, oxadiargyl and oxadiazon;
phenoxy herbicides such as bromofenoxim, clomeprop, 2,4-DEB, 2,4-DEP, difenopenten, disul, erbon, etnipromid, fenteracol and trifopsime;
aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop;
phenylenediamine herbicides such as dinitramine, and prodiamine
phenyl pyrazolyl ketone herbicides such as benzofenap, pyrasulfotole, pyrazolynate, pyrazoxyfen and topramezone;
pyrazolylphenyl herbicides such as fluazolate, nipyraclofen and pyraflufen;
pyridazine herbicides such as credazine, pyridafol and pyridate;
pyridazinone herbicides such as brompyrazon, chloridazon, dimidazon, flufenpyr, metflurazon, norflurazon, oxapyrazon and pydanon;
pyridine herbicides such as aminopyralid, cliodinate, clopyralid, dithiopyr, fluroxypyr, haloxydine, picloram, picolinafen, pyriclor, thiazopyr and triclopyr;
pyrimidinediamine herbicides such as iprymidam and tioclorim;
quaternary ammonium herbicides such as cyperquat, diethamquat, difenzoquat, diquat, morfamquat and paraquat;
thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate;
thiocarbonate herbicides such as dimexano, EXD, proxan and eptam (EPTC);
thiourea herbicides such as methiuron;
triazine herbicides such as dipropetryn; triaziflam and trihydroxytriazine;
chlorotriazine herbicides such as atrazine; chlorazine, cyanazine, cyprazine, eglinazine, ipazine, mesoprazine, procyazine, proglinazine, propazine, sebuthylazine, simazine, terbuthylazine and trietazine;
methoxytriazine herbicides such as atraton, methometon, prometon, secbumeton, simeton and terbumeton;
methylthiotriazine herbicides such as ametryn, aziprotryne, cyanatryn, desmetryn, dimethametryn, methoprotryne, prometryn, simetryn and terbutryn;
triazinone herbicides such as ametridione, amibuzin, hexazinone, isomethiozin, metamitron and metribuzin;
triazole herbicides such as amitrole, cafenstrole, epronaz and flupoxam;
triazolone herbicides such as amicarbazone, bencarbazone, carfentrazone, flucarbazone, propoxycarbazone and sulfentrazone;
triazolopyrimidine herbicides such as cloransulam, diclosulam, florasulam, flumetsulam, metosulam and penoxsulam;
uracil herbicides such as butafenacil, bromacil, flupropacil, isocil, lenacil and terbacil;
urea herbicides such as benzthiazuron, cumyluron, cycluron, dichloralurea, diflufenzopyr, isonoruron, isouron, methabenzthiazuron, monisouron and noruron;
phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron;
sulfonylurea herbicides including:
pyrimidinylsulfonylurea herbicides such as amidosulfuron; azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron;
triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; and thiadiazolylurea herbicides such as buthiuron, ethidimuron, tebuthiuron, thiazafluron and thidiazuron; and unclassified herbicides such as KIH-485, acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate endothal, fluoromidine, fluridone, flurochloridone, flurtamone, fluthiacet, indanofan, methyl isothiocyanate, OCH, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

The weight ratio of phenoxy-alkanoic acid to other herbicide will depend on the nature of the other herbicide and desired loading. However, typically the weight ratio of phenoxy-alkanoic acid to other herbicide (or herbicides) is in the range of from 30:1 to 1:10. It is generally preferred that the phenoxy-alkanoic acid herbicide constitutes more than 15% w/w of the total herbicide content and preferably at least 75% w/w of the total herbicide content. In one embodiment the mixture with other herbicides comprises more than 50% w/w of the total herbicide content of 2,4-D and preferably at least 75% w/w 2,4-D and most preferably at least 80% w/w 2,4-D.

In one set of embodiments the composition comprises a phenoxy-alkanoic acid herbicide and a pyridine auxin herbicide such as picloram, clopyralid, triclopyr, fluroxypyr, aminopyralid or mixtures of two or more thereof. Typically the weight ratio of phenoxy-alkanoic acid to pyridine auxin herbicide (or herbicides) is in the range of from 30:1 to 1:10. Preferably the pyridine auxin herbicide will be in the form of the acid. In a further set of embodiments the composition comprises a phenoxyalkanoic acid herbicide and glyphosate (preferably in the form of glyphosate acid) in a weight ratio in the range of from 30:1 to 1:10.

In a further set of embodiments the emulsifiable concentrate comprises a mixture of the phenoxy-alkanoic acid herbicide and an aryloxyphenoxy-alkanoic acid herbicide, preferably selected from the group consisting of fenoxaprop, fenoxaprop-P, haloxyfop and mixtures thereof. The weight ratio of phenoxy-alkanoic acid to aryloxyphenoxyalkanoic acid herbicide (or herbicides) is preferably in the range of from 30:1 to 1:10.

The emulsifiable concentrate composition is typically in the form of solution, however in some embodiments additional components such as further active agents may be present as may be present as a solid suspension in the concentrate.

The invention will now be described with reference to the following Examples. It is to be understood that the Examples are provided by way of illustration of the invention and that they are in no way limiting to the scope of the invention.

EXAMPLES

Examples 1 to 4 (E1 to E4)

The compositions of these examples were prepared by combining the components shown in Table 1 in accordance with a process comprising the following steps in sequence:

Step 1: Weight all excipients (excluding the Amine) into a 250 ml beaker.
Step 2: Add a magnetic flea to the beaker, place beaker on a hot plate, commence stirring and heat to 75 Deg. C.
Step 3: Continue heating at 75 Deg. C while stirring for approximately 1.0 hour or until all solids have dissolved.
Step 4: Continue heating at 75 Deg. C while stirring add the Amine slowly.

TABLE 1

| Material name | E1 (g) | E2 g |
| --- | --- | --- |
| 2,4-D acid (97.7%) | 41 | 41 |
| KEMMAT HF60 | 4 | 4 |
| TERMUL 1284 | 6 | 6 |
| TOXIMUL 8320 | 5 | 5 |
| Triethanolamine (TEA) 85% | 5 | Nil |
| Tri-isopropanol-amine (TIPA) 85% | Nil | 5 |
| Diethanolamine (DEA) 85% | Nil | Nil |
| Mono-ethanol-amine (MEA) 99% | Nil | Nil |
| Surfonic AGM-550 | Nil | Nil |
| SOLVESSO 200 | 10 | 10 |
| Hallcomid 8-10 | To 100 g (29 g) | To 100 g (29 g) |
| Observations | After 1.0 hr of stirring & heating @ 75 Deg. C. all solids dissolve. Stable after 24 hrs @ RT. | After 1.0 hr of stirring & heating @ 75 Deg. C. all solids dissolve. Stable after 24 hrs @ RT. |
| Emulsion Stability (CIPAC MT36.1) (5/95 dilution in CIPAC STD D water) | Very good bloom. 30 min Stable (Nil cream) 2 hrs: Stable (Nil cream) 4 hrs: Stable (Nil cream) 24 hrs: Stable (Nil cream) | Very good bloom. 30 min: Stable (Nil cream) 2 hrs: Stable (Nil cream) 4 hrs: 0.2 ml cream 24 hrs: 1 ml cream |
| Comments | 24 hrs @ RT & 0 Deg C. No crystallization occurs after 7 days @ 0 Deg. C. (with seeding). D (20 Deg. C.) = 1.128 g/ml | 24 hrs @ RT & 0 Deg. C. No crystallization occurs after 7 days @ 0 Deg. C. (with seeding). D (20 Deg. C.) = 1.222 g/ml |

| Material name | E3 (g) | E4 (g) |
| --- | --- | --- |
| 2,4-D acid (97.7%) | 41 | 41 |
| KEMMAT HF60 | 4 | 4 |
| TERMUL 1284 | 6 | 6 |

TABLE 1-continued

|  |  |  |
|---|---|---|
| TOXIMUL 8320 | 5 | 5 |
| Triethanolamine (TEA) 85% | 5 | 5 |
| Tri-isopropanol-amine (TIPA) 85% | Nil | Nil |
| Diethanolamine (DEA) 85% | Nil | Nil |
| Mono-ethanol-amine (MEA) 99% | Nil | Nil |
| Surfonic AGM-550 | 5 | 10 |
| SOLVESSO 200 | 10 | 10 |
| Hallcomid 8-10 | To 100 g (24 g) | To 100 g (19 g) |
| Observations | After 1.0 hr of stirring & heating @ 75 Deg. C. all solids dissolve. Stable after 24 hrs @ RT. Very good bloom. | After 1.0 hr of stirring & heating @ 75 Deg. C. all solids dissolve. Stable after 24 hrs @ RT. Very good bloom. |
| Emulsion Stability (CIPAC MT36.1) (5/95 dilution in CIPAC STD D water) | 30 min: Stable (Nil cream) 2 hrs: Stable (Nil cream) 4 hrs: Stable (Nil cream) 24 hrs: Stable (Nil cream) | 30 min: Stable (Nil cream) 2 hrs: Stable (Nil cream) 4 hrs: Stable (Nil cream) 24 hrs: Stable (Nil cream) |
| Comments | 24 hrs @ RT & 0 Deg. C. No crystallization occurs after 7 days @ 0 Deg. C. (with seeding). D (20 Deg. C.) = 1.137 g/ml | 24 hrs @ RT & 0 Deg. C. No crystallization occurs after 7 days @ 0 Deg. C. (with seeding). D (20 Deg. C.) = 1.139 g/ml |

Examples 5 to 9

The compositions of these examples were prepared by combining the components as specified in Table 2 with a process involving the following steps on sequence:
Step 1: Weigh all excipients (excluding the Amine) into a 250 ml beaker.
Step 2: Add a magnetic flea to the beaker, place beaker on a hot plate, commence stirring and heat to 75 Deg. C.
Step 3: Continue heating at 75 Deg. C while stirring for approximately 1.0 hour or until all solids have dissolved.
Step 4: Continue heating at 75 Deg. C while stirring add the Amine slowly.

Example 10—40% 2,4-D Acid EC (4% TEA99%+2% Water)

The composition shown in Table 3 was prepared using the manufacturing method described and resulted in the properties shown in Table 4.

TABLE 3

| 40% w/w 2,4-D acid EC. | 2,4-D acid 97.6% | 205.0 g |
|---|---|---|
|  | LABS acid | 20.0 g |
|  | TOXIMUL 8320 | 35.0 g |
|  | TEA 99% | 20.0 g |

TABLE 4

| Material name | E5 (g) | E6 (g) | E7 (g) | E8 (g) | E9 (g) |
|---|---|---|---|---|---|
| 2,4-D acid (97.7%) | 41 | 41 | 41 | 41 | 41 |
| KEMMAT HF60 | 4 | 5 | 3 | 4 | 4 |
| TERMUL 1284 | 4 | 5 | 5 | 6 | 5 |
| TOXIMUL 8320 | 4 | 5 | 4 | 5 | 3 |
| SOLVESSO 200 | 10 | F10 | 10 | 10 | 10 |
| Amine (TIPA 85%) | 3 | Nil | Nil | Nil | Nil |
| Amine (TEA 85%) | Nil | 3 | 3 | 3 | 3 |
| Hallcomid 8-10 | To 100 g (34 g) | To 100 g (31 g) | To 100 g (34 g) | To 100 g (31 g) | To 100 g (34 g) |
| Observations | After 1.0 hr of stirring & heating @ 75 Deg. C. all solids dissolve. | After 1.0 hr of stirring & heating @ 75 Deg. C. all solids dissolve. | After 1.0 hr of stirring & heating @ 75 Deg. C. all solids dissolve. | After 1.0 hr of stirring & heating @ 75 Deg. C. all solids dissolve. | After 1.0 hr of stirring & heating @ 75 Deg. C. all solids dissolve. |
| Comments | Emulsification stability (5/95 in STD D water) is v. good (V. good bloom). 30 min: ~0.2 ml cream; 2 hrs: ~0.5 ml cream; 4 hrs: ~1 ml cream; 24 hrs: ~3 ml cream. Easily re-emulsifies after 10 inversions. No crystallization occurs after 24 hrs @ RT & 0 Deg. C. No crystallization occurs after 7 days @ 0 Deg. C. (with seeding). | Emulsification stability (5/95 in STD D water) is v. good (V. good bloom). 30 min: ~0.2 ml cream; 2 hrs: ~0.5 ml cream; 4 hrs: ~1 ml cream; 24 hrs: ~3 ml cream. Easily re-emulsifies after 10 inversions. No crystallization occurs after 24 hrs @ RT & 0 Deg. C. No crystallization occurs after 7 days @ 0 Deg. C. (with seeding). | Emulsification stability (5/95 in STD D water) is v. good (V. good bloom). 30 min: stable; 2 hrs: stable; 4 hrs: stable; 24 hrs: ~0.5 ml cream. Easily re-emulsifies after 10 inversions. No crystallization occurs after 24 hrs @ RT & 0 Deg. C. No crystallization occurs after 7 days @ 0 Deg. C. (with seeding). | Emulsification stability (5/95 in STD D water) is v. good (V. good bloom). 30 min: stable; 2 hrs: stable; 4 hrs: stable; 24 hrs: stable. No crystallization occurs after 7 days @ 0 Deg. C. (with seeding). | Emulsification stability (5/95 in STD D water) is v. good (V. good bloom). 30 min: ~0.2 ml cream; 2 hrs: ~0.5 ml cream; 4 hrs: ~1 ml cream; 24 hrs: ~3.5 ml cream. Easily re-emulsifies after 10 inversions. No crystallization occurs after 24 hrs @ RT & 0 Deg. C. No crystallization occurs after 7 days @ 0 Deg. C. (with seeding). |

TABLE 3-continued

| | |
|---|---|
| SOLVESSO 200 | 50.0 g |
| Water | 10.0 g |
| Hallcomid 8-10 | 160.0 g |

Manufacturing Method

Step 1: Weigh 60% of the SOLVESSO 200 the LABS acid, TOXIMUL 8320 into a 250 ml beaker (vessel 1).

Step 2: Add a magnetic flea to the beaker, place beaker on a stirrer, commence stirring & add amine slowly (exothermic).

Step 3: Continue stirring at 40° C. for 10 min or until a homogenous mixture is obtained.

Step 4: Weigh the 2,4-D acid & the Hallcomid 8-10 & 40% of SOLVESSO 200 into a 1 L beaker (vessel 2).

Step 5: Place beaker on a hot plate, commence stirring with an overhead mixer & heat to 65° C.

Step 6: Continue heating at 65° C. while stirring for ~30 min or until a homogenous mixture is obtained.

Cool the contents of vessel 2 to 50° C.

Step 7: While stirring vessel 2 (at 50° C.), add contents of vessel 1 slowly to vessel 2. Commence cooling.

Step 8: Continue to cool, stir the contents of vessel 2 for 10 min, cool to 20° C. and add the water slowly.

Step 9: Continue stirring for ~10 min at 20° C.

Step 10: Filter the formulation through 100 micron GAF filter.

RESULTS - Table 4

| Parameters | INITIAL | 2 w at 54° C. |
|---|---|---|
| Appearance | Yellow clear liquid | Yellow clear liquid |
| Active content (2,4-D), g/kg | 395.6 | 388.6 |
| Density (20° C.), g/ml | 1.121 | 1.121 |
| pH (1% dilution in DI water) | 3.12 | 3.14 |
| Emulsion Stability (CIPAC MT36.1) CIPAC STD A water | Very good emulsification. | Very good emulsification. |
| % Oil (30 min; 2 h; 24 hrs) | (0; 0; 0) | (0; 0; 0) |
| % cream (30 min; 2 h; 24 hrs) CIPAC STD D water | (0; 0; 0.5) | (0; 0; 0.5) |
| % Oil (30 min; 2 h; 24 hrs) | (0; 0; 0) | (0; 0; 0) |
| % cream (30 min; 2 h; 24 hrs) Low temp storage stab. (CIPAC MT39.3) | (0; 0; 0.5) | (0.2; 0.4; 0.8) |
| 24 hrs: | | Stable. No crystallization. |
| 7 days (seeding): | | Stable. No crystallization. |

The composition was found to meet all the parameters required for this product with excellent emulsification stability. The active content was found to be within specification initially and after accelerated storage stability (initial: 395.6 g/L 2,4-D acid; After 2 weeks @ 54° C.: 388.6 g/L 2,4-D acid).

Example 11—40% 2,4-D Acid EC (4% Methoxypropylamine (MOPA)+2% Water

The composition shown in Table 5 was prepared using the manufacturing method described and resulted in the properties described in Table 6.

TABLE 5

| | | |
|---|---|---|
| 40% w/w 2,4-D acid EC. | 2,4-D acid 97.6% | 205.0 g |
| | LABS acid | 20.0 g |
| | TOXIMUL 8320 | 35.0 g |
| | methoxypropylamine (MOPA) | 20.0 g |
| | Water | 10.0 g |
| | SOLVESSO 200 | 50.0 g |
| | Hallcomid 8-10 | 160.0 g |

Manufacturing Method

Step 1: Weigh 60% of the SOLVESSO 200 the LABS acid, TOXIMUL 8320 into a 250 ml beaker (vessel 1).

Step 2: Add a magnetic flea to the beaker, place beaker on a stirrer, commence stirring & add amine slowly (exothermic).

Step 3: Continue stirring at 40° C. for 10 min or until a homogenous mixture is obtained.

Step 4: Weigh the 2,4-D acid & the Hallcomid 8-10 & 40% of SOLVESSO 200 into a 1 L beaker (vessel 2).

Step 5: Place beaker on a hot plate, commence stirring with an overhead mixer & heat to 65° C.

Step 6: Continue heating at 65° C. while stirring for ~30 min or until a homogenous mixture is obtained.

Cool the contents of vessel 2 to 50° C.

Step 7: While stirring vessel 2 (at 50° C.), add contents of vessel 1 slowly to vessel 2. Commence cooling.

Step 8: Mix the contents of vessel 2 for a further 10 min and while mixing, add the water slowly.

Step 9: Continue stirring for ~10 min and cool the mixture to 20° C.

Step 10: Filter the formulation through 100 micron GAF filter.

TABLE 6

RESULTS

| Parameters | INITIAL | 2 w at 54° C. |
|---|---|---|
| Appearance | Yellow clear liquid | Yellow clear liquid |
| Active content (2,4-D), g/kg | 400 | 393 |
| Density (20° C.), g/ml | 1.11 | 1.115 |
| pH (1% dilution in DI water) | 3.34 | 3.29 |
| Emulsion Stability (CIPAC MT36.1) CIPAC STD A water | Very good emulsification. | Very good emulsification. |
| % Oil (30 min; 2 h; 4 hrs) | (0; 0; 0) | (0; 0; 0) |
| % cream (30 min; 2 h; 4 hrs) CIPAC STD D water | (0.3; 0.5; 0.7) | (0; 0.3; 0.5) |
| % Oil (30 min; 2 h; 4 hrs) | (0; 0; 0) | (0; 0; 0) |
| % cream (30 min; 2 h; 4 hrs) Low temp storage stab. (CIPAC MT39.3) | (0.5; 0.6; 1.0) | (0.2; 0.5; 0.6) |
| 24 hrs: | | Stable. No crystallization. |
| 7 days (seeding): | | Stable. No crystallization. |

The active content was found to be within specification initially and after the accelerated storage stability (initial: 400.0 g/L 2,4-D acid; After 2 weeks @ 54° C.: 393.0 g/L 2,4-D acid).

Example 12—40% 2,4-D Acid EC (2% TEA+2% MOPA+2% Water)

The composition of Example 12 was prepared from components shown in Table 7 using the procedure shown below and provided a composition having the properties detailed in Table 8.

TABLE 9

| 40% w/w 2,4-D acid EC. | 2,4-D acid 98.78% | 202.5 g |
|---|---|---|
|  | LABS acid | 20.0 g |
|  | TOXIMUL 8320 | 35.0 g |
|  | TEA 99% | 10.0 g |
|  | MOPA | 10.0 g |
|  | SOLVESSO 200 | 50.0 g |
|  | Water | 10.0 g |
|  | Hallcomid 8-10 | 162.5 g |

Manufacturing Method

Step 1: Weigh 60% of the SOLVESSO 200 the LABS acid, TOXIMUL 8320 into a 250 ml beaker (vessel 1).
Step 2: Add a magnetic flea to the beaker, place beaker on a stirrer, commence stirring & add amines slowly (exothermic).
Step 3: Continue stirring at 40° C. for 10 min or until a homogenous mixture is obtained.
Step 4: While stirring (at 40° C.), add water slowly. Mix for ~20 min.
Step 5: Weigh the 2,4-D acid & the Hallcomid 8-10 & 40% of SOLVESSO 200 into a 1 L beaker (vessel 2).
Step 6: Place beaker on a hot plate, commence stirring with an overhead mixer & heat to 65° C.
Step 7: Continue heating at 65° C. while stirring for ~60 min or until a homogenous mixture is obtained. Cool the contents of vessel 2 to 50° C.
Step 8: While stirring vessel 2 (at 50° C.), add contents of vessel 1 slowly to vessel 2.
Step 9: Continue stirring for a further 20 min and cool to 20° C.
Step 10: Filter the formulation through 100 micron GAF filter.

TABLE 8

RESULTS

| Parameters | INITIAL | 2 w at 54° C. |
|---|---|---|
| Appearance | Yellow clear liquid | Yellow clear liquid |
| Active content (2,4-D), g/kg | 392 | 390 |
| Density (20° C.), g/ml | 1.119 | 1.119 |
| pH (1% dilution in DI water) | 3.18 | 3.29 |
| Emulsion Stability (CIPAC MT36.1) CIPAC STD A water | Very good emulsification. | Very good emulsification. |
| % Oil (30 min; 2 h; 24 hrs) | (0; 0; 0) | (0; 0; 0) |
| % cream (30 min; 2 h; 24 hrs) CIPAC STD D water | (0; 0; 1.0) | (0.2; 0.4; 1.5) |
| % Oil (30 min; 2 h; 24 hrs) | (0; 0; 0) | (0; 0; 0) |
| % cream (30 min; 2 h; 24 hrs) Low temp storage stab. (CIPAC MT39.3) | (0; 0; 1.0) | (0.3; 0.6; 1.6) |
| 24 hrs: | Stable. No crystallization. | |
| 7 days (seeding): | Stable. No crystallization. | |

The active content was found to be within specification initially and after the accelerated storage stability (initial: 392.0 g/L 2,4-D acid; After 2 weeks @ 54° C.: 390.0 g/L 2,4-D acid).

Example 13—40% MCPA Acid EC (4% (Methoxypropylamine) MOPA+2% Water)

The composition shown in Table 9 was prepared by the manufacturing method described and the resulting properties of the composition are set out in Table 10.

TABLE 9

| 40% w/w MCPA acid EC. | MCPA acid 96% | 208.3 g |
|---|---|---|
|  | LABS acid | 13.0 g |
|  | TERMUL 1284 | 20.0 g |
|  | TOXIMUL 8320 | 17.0 g |
|  | MOPA | 20.0 g |
|  | SOLVESSO 200 | 50.0 g |
|  | Water | 10.0 g |
|  | Hallcomid 8-10 | 161.7 g |

Manufacturing Method

Step 1: Weigh 60% of the SOLVESSO 200 the LABS acid+TOXIMUL 8320+TERMUL 1284 into a 250 ml beaker (vessel 1).
Step 2: Add a magnetic flea to the beaker, place beaker on a stirrer, commence stirring & add amine slowly (exothermic).
Step 3: Continue stirring at 40° C. for 30 min or until a homogenous mixture is obtained.
Step 4: While continuing to mix, add the water slowly.
Step 5: Weigh the MCPA acid & the Hallcomid 8-10 & 40% of SOLVESSO 200 into a 1 L beaker (vessel 2).
Step 6: Place beaker on a hot plate, commence stirring with an overhead mixer & heat to 65° C.
Step 7: Continue heating at 65° C. while stirring for ~30 min or until a homogenous mixture is obtained. Cool the contents of vessel 2 to 50° C.
Step 8: While stirring vessel 2 (at 50° C.), add contents of vessel 1 slowly to vessel 2. Commence cooling.
Step 9: Continue stirring for ~10 min and cool the mixture to 20° C.
Step 10: Filter the formulation through 100 micron GAF filter.

TABLE 10

RESULTS

| Parameters | INITIAL | 2 w at 54° C. |
|---|---|---|
| Appearance | Yellow/amber coloured liquid. | Yellow/amber coloured liquid. |
| Active content (MCPA), g/kg | 413 | 402 |
| Density (20° C.), g/ml | 1.075 | 1.074 |
| pH (1% dilution in DI water) | 3.5 | 3.52 |
| Emulsion Stability (CIPAC MT36.1) CIPAC STD A water | Very good emulsification. | Very good emulsification. |
| % Oil (30 min; 2 h; 4 hrs) | (0; 0; 0) | (0; 0; 0) |
| % cream (30 min; 2 h; 4 hrs) CIPAC STD D water | (0.8; 1.8; 2.0) | (1.5; 2.5; 4.0) |
| % Oil (30 min; 2 h; 4 hrs) | (0; 0; 0) | (0; 0; 0) |
| % cream (30 min; 2 h; 4 hrs) | (0.8; 2.0; 2.2) | (1.5; 3.0; 5.0) |

23

TABLE 10-continued

| Parameters | INITIAL | 2 w at 54° C. |
|---|---|---|
| Low temp storage stab. (CIPAC MT39.3) | | |
| 24 hrs: | | Stable. No crystallization. |
| 7 days (seeding): | | Stable. No crystallization. |

24

The active content was found to be within specification initially and after the accelerated storage stability (initial: 413.0 g/L MCPA acid; After 2 weeks @ 54° C.: 402.0 g/L MCPA acid).

Examples 14-17 2,4-D Acid EC Concentrates

Emulsifiable concentrate compositions containing 2,4-D in accordance with Table 11 were prepared using the Manufacturing Method described.

TABLE 11

| | Formulation ID | |
|---|---|---|
| Material name | E14 (g) | E15 (g) |
| 2,4-D acid (97.6%) | 410 | 410 |
| Calsogen AR100 (40% CaTetrapropyleneBS + 10% Fatty alcohol polyglycol ether 6-15EO in Solvent Naptha (petroleum), heavy aromatic | Nil | Nil |
| LABS acid (Linear Alkyl Benzene Sulphonic Acid) | 40 | 40 |
| TOXIMUL 8320 (>=90% Polyethylene-Polypropylene glycol monobutyl ether) | 70 | 70 |
| Triethanolamine (TEA) 99% | 50 | 40 |
| Methoxypropylamine (MOPA) | Nil | Nil |
| SOLVESSO 200 (Solvent Naphtha (petroleum), heavy aromatic) | 100 | 100 |
| Water | 10 | 20 |
| Hallcomid 8-10 (N,N-dimethyl-Octamide 40-70% + N,N-dimethyl-Decamide 30-60% | to 1000 g (320 g) | to 1000 g (320 g) |
| Manufacturing method | 2 | 2 |
| Observations/Comments | Formulated using a different manufacturing method and an alternative emulsifier system and using 5% TEA + 1% water. Formulation meets specification for Emulsifiable Concentrate products. Based on the assay results, transformation reactions are still occurring. | As per E14 but formulated using 4% TEA + 2% water. Formulation meets specification for Emulsifiable Concentrate products, including active content. |
| Appearance (Initial) | Yellow, clear liquid | Yellow, clear liquid |
| Appearance (after 2 W @ 54°) | Yellow, clear liquid | Yellow, clear liquid |
| Active content (2,4-D), g/kg (Initial) | 390 | 396 |
| Active content (2,4-D), g/kg (after 2 W @ 54° C.) | 381 | 389 |
| Density (20° C.), g/ml (Initial) | 1.122 | 1.121 |
| Density (20° C.), g/ml (after 2 W @ 54° C.) | 1.122 | 1.121 |
| pH (1% diln in DI water) (Initial) | 3.18 | 3.12 |
| pH (1% diln in DI water) (after 2 W @ 54° C.) | 3.15 | 3.14 |
| INITIAL Emulsion Stability (CIPAC MT36.1) CIPAC STD A water | Very good emulsification | Very good emulsification |
| % Oil (30 min; 2 h; 24 hrs) | (0; 0; 0) | (0; 0; 0) |
| % cream (30 min; 2 h; 24 hrs) | (0; 0; 0.1) | (0; 0; 0.5) |
| CIPAC STD D water | | |
| % Oil (30 min; 2 h; 24 hrs) | (0; 0; 0) | (0; 0; 0) |
| % cream (30 min; 2 h; 24 hrs) | (0; 0; 0.1) | (0; 0; 0.5) |
| After 2 weeks @ 54° C. | Very good emulsification. | Very good emulsification. |

TABLE 11-continued

| | | |
|---|---|---|
| Emulsion Stability (CIPAC MT36.1) CIPAC STD A water | | |
| % Oil (30 min; 2 h; 24 hrs) | (0; 0; 0) | (0; 0; 0) |
| % cream (30 min; 2 h; 24 hrs) | (0; 0; 0.5) | (0; 0; 0.5) |
| CIPAC STD D water | | |
| % Oil (30 min; 2 h; 24 hrs) | (0; 0.4; 0.8) | (0; 0; 0) |
| % cream (30 min; 2 h; 24 hrs) | (0; 0.4; 0.8) | (0.2; 0.4; 0.8) |
| Low temp storage stab. (CIPAC MT39.3) | | |
| 24 hrs: | Stable. No crystallization. | Stable. No crystallization. |
| 7 days (seeding): | Stable. No crystallization. | Stable. No crystallization. |

| | Formulation ID | |
|---|---|---|
| Material name | E16 (g) | E17 (g) |
| 2,4-D acid (97.6%) | 410 | 405 (2,4-D acid 98.78%) |
| Calsogen AR100 (40% CaTetrapropyleneBS + 10% Fatty alcohol polyglycol ether 6-15EO in Solvent Naptha (petroleum), heavy aromatic | Nil | Nil |
| LABS acid (Linear Alkyl Benzene Sulphonic Acid) | 40 | 40 |
| TOXIMUL 8320 (>=90% Polyethylene-Polypropylene glycol monobutyl ether) | 70 | 70 |
| Triethanolamine (TEA) 99% | Nil | 20 |
| Methoxypropylamine (MOPA) | 40 | 20 |
| SOLVESSO 200 (Solvent Naphtha (petroleum), heavy aromatic) | 100 | 100 |
| Water | 20 | 20 |
| Hallcomid 8-10 (N,N-dimethyl-Octamide 40-70% + N,N-dimethyl-Decamide 30-60% | to 1000 g (320 g) | to 1000 g (325 g) |
| Manufacturing method | 2 | 2 |
| Observations/Comments | Formulated using 4% MOPA + 2% water. Active content reminas stable. meets specification for Emulsifiable Concentrate products. | Formulated using 2% MOPA + 2% TEA + 2% water. Active content remains stable. Meets specification for Emulsifiable Concentrate products. |
| Appearance (Initial) | Yellow, clear liquid | Yellow, clear liquid |
| Appearance (after 2 W @ 54°) | Yellow, clear liquid | Yellow, clear liquid |
| Active content (2,4-D), g/kg (Initial) | 400 | 392 |
| Active content (2,4-D), g/kg (after 2 W @ 54° C.) | 393 | 390 |
| Density (20° C.), g/ml (Initial) | 1.11 | 1.119 |
| Density (20° C.), g/ml (after 2 W @ 54° C.) | 1.115 | 1.119 |
| pH (1% diln in DI water) (Initial) | 3.34 | 3.18 |
| pH (1% diln in DI water) (after 2 W @ 54° C.) | 3.29 | 3.29 |
| INITIAL Emulsion Stability (CIPAC MT36.1) CIPAC STD A water | Very good emulsification | Very good emulsification |
| % Oil (30 min; 2 h; 24 hrs) | (0; 0; 0) | (0; 0, 0) |
| % cream (30 min; 2 h; 24 hrs) | (0.3; 0.5; 0.7) | (0; 0; 1.0) |
| CIPAC STD D water | | |
| % Oil (30 min; 2 h; 24 hrs) | (0; 0; 0) | (0; 0; 0) |
| % cream (30 min; 2 h; 24 hrs) | (0.5; 0.6; 1.0) | (0; 0; 1.0) |
| After 2 weeks @ 54° C. Emulsion Stability (CIPAC MT36.1) CIPAC STD A water | Very good emulsification. | Very good emulsification. |
| % Oil (30 min; 2 h; 24 hrs) | (0; 0; 0) | (0; 0; 0) |
| % cream (30 min; 2 h; 24 hrs) | (0; 0.3; 0.5) | (0.2; 0.4; 1.5) |

TABLE 11-continued

| CIPAC STD D water | | |
|---|---|---|
| % Oil (30 min; 2 h; 24 hrs) | (0; 0; 0) | (0; 0; 0) |
| % cream (30 min; 2 h; 24 hrs) | (0.2; 0.5; 0.6) | (0.3; 0.6; 1.6) |
| Low temp storage stab. (CIPAC MT39.3) | | |
| 24 hrs: | Stable. No crystallization. | Stable. No crystallization. |
| 7 days (seeding): | Stable. No crystallization. | Stable. No crystallization. |

Manufacturing Method 1
Step 1: Weight the CALSOGEN AR100, TOXIMUL 8320 & 40% of SOLVESSO 200 into a 250 ml beaker (vessel 1).
Step 2: Add a magnetic flea to the beaker, place baker on a stirrer, commence stirring & heat to 40° C.
Step 3: Continue stirring for 30 min or until a homogenous mixture is obtained.
Step 4: Weigh the 2,4-D acid & the Hallcomid 8-10 & 60% of SOLVESSO 200 into a 1 L beaker (vessel 2).
Step 5: Place beaker on a hot plate, commence stirring with an overhead mixer & heat to 75° C.
Step 6: Continue heating at 75° C. while stirring for ~60 min or until a homogenous mixture is obtained. Cool the mixture to 40° C.
Step 7: While stirring vessel 2 (at 40° C.), add contents of vessel 1 slowly to vessel 2.
Step 8: Continue stirring for ~30 min or until a homogenous mixture is obtained.
Cool the mixture to 20° C. & filter through 100 micron filter.
Manufacturing Method 2
Step 1: Weigh 60% of the SOLVESSO 200 the LABS acid, TOXIMUL 8320 into a 250 ml beaker (vessel 1).
Step 2: Add a magnetic flea to the beaker, place beaker on a stirrer, commence stirring & add amine slowly (exothermic).
Step 3: Heat to 50° C. and continue stirring for 30 min or until a homogenous mixture is obtained.
Step 4: Weigh the 2,4-D acid & the Hallcomid 8-10 & 40% of SOLVESSO 200 into a 1 L beaker (vessel 2).
Step 5: Place beaker on a hot plate, commence stirring with an overhead mixer & heat to 65° C.
Step 6: Continue heating at 65° C. while stirring for ~30 min or until a homogenous mixture is obtained. Cool the contents of vessel 2 to 50° C.
Step 7: While stirring vessel 2 (at 50° C.), add contents of vessel 1 slowly to vessel 2. Commence cooling.
Step 8: Continue stirring the contents of vessel 2 for 10 min, cool to 20° C. and add the water slowly.
Step 9: Continue stirring for ~10 min at 20° C.
Step 10: Filter the formulation through 100 micron GAF filter.

Examples 18-21—MCPA EC Compositions

Emulsifiable concentrates containing MCPA were prepared having the composition set out in Table 12 using manufacturing method 1 or 2 shown below the Table.

TABLE 12

| | Formulation ID | | | |
|---|---|---|---|---|
| Material name | E18 (g) | E19 (g) | E20 (g) | E21 (g) |
| MCPA acid (97.0%) | 412 | 412 | 417 (MCPA acid 96%) | 417 (MCPA acid 96%) |
| LABS acid (Linear Alkyl Benzene Sulphonic Acid) | 26 | 26 | 26 | 26 |
| TERMUL 1284 (>60% Castor Oil Ethoxylate) | 40 | 40 | 40 | 40 |
| TOXIMUL 8320 (>= 90% Polyethylene-polypropylene glycol monobutyl ether) | 34 | 34 | 34 | 34 |
| Triethanolamine (TEA) 85% | 20 | 30 | Nil | Nil |
| Mono-ethanolamine (MEA) 99% | Nil | Nil | Nil | 20 |
| Methoxypropylamine (MOPA) 100% | Nil | Nil | 40 | 20 |
| Water | Nil | Nil | 20 | 20 |
| SOLVESSO 200 (Solvent Naphtha (petroleum), heavy aromatic) | 100 | 100 | 100 | 100 |
| Hallcomid 8-10 (N,N-dimethyl-Octamide 40-70% + N,N-dimethyl-Decamide 30-60%) | to 1000 g (368 g) | to 1000 g (358 g) | to 1000 g (323 g) | to 1000 g (323 g) |
| Manufacturing method | 1 | 1 | 2 | 2 |
| Observations/Comments | Formulation meets specification for Emulsifiable Concentrate products, some reduction in active content over 2 weeks. | Formulation meets specification for Emulsifiable Concentrate products, some reduction in active content over 2 weeks. | Formulation meets the specification for Emulsifiable Concentrate products including active content. The emulsification stability of the product is not ideal, however, it is within the specification limits for emulsifiable concentrates as the APVMA guidelines. | Formulation meets specification for Emulsifiable Concentrate products composition shows reduced active content after acc. Storage stability (2 weeks @54° C.). |

TABLE 12-continued

| Material name | Formulation ID | | | |
|---|---|---|---|---|
| | E18 (g) | E19 (g) | E20 (g) | E21 (g) |
| Appearance (Initial) | Yellow, clear liquid | Yellow, clear liquid | Yellow/amber clear liquid | Yellow, slightly hazy liquid |
| Appearance (after 2 W @ 54° C.) | Yellow, clear liquid | Yellow, clear liquid | Yellow/amber clear liquid | Yellow, slightly hazy liquid |
| Active content (2,4-D), g/kg (Initial) | 390 | 389 | 413 | 404 |
| Active content (2,4-D), g/kg (after 2 W @ 54° C.) | 383 | 382 | 402 | 376 |
| Density (20° C.), g/ml (Initial) | 1.066 | 1.07 | 1.075 | 1.074 |
| Density (20° C.), g/ml (after 2 W @ 54° C.) | 1.066 | 1.07 | 1.074 | 1.074 |
| pH (1% diln in DI water) (Initial) | 3.12 | 3.2 | 3.5 | 3.61 |
| pH (1% diln in DI water) (after 2 W @ 54° C.) | 3.15 | 3.24 | 3.52 | 3.59 |
| (INITIAL) Emulsion Stability (CIPAC MT36.1) | Good emulsification. | Very good emulsification. | Good emulsification. | Good emulsification. |
| % Oil (30 min) | (0) | (0) | (0) | (0) |
| % cream CIPAC STD A Water (30 min) | (1.5) | (0) | (0.8) | (0) |
| % Oil (30 min) | (0) | (0) | (0) | (0) |
| % cream CIPAC STD D Water (30 min) | (0) | (0) | (0.8) | (0) |
| AFTER 2 W @ 54° C. Emulsion Stability (CIPAC MT36.1) CIPAC STD A water | Poor emulsification | Poor emulsification | Good emulsification | Good emulsification |
| % Oil (30 min) | (0) | (0) | (0) | (0) |
| % cream (30 min) | (5) | (6) | (1.5) | (0) |
| CIPAC STD D water | | | | |
| % Oil (30 min) | 0 | (0) | (0) | (0) |
| % cream (30 min) | (7) | (7) | (1.5) | (0.2) |
| Low temp storage stab. (CIPAC MT39.3) | | | | |
| 24 hrs: | Stable. No crystallization. | Stable. No crystallization. | Stable. No crystallization. | Stable, No crystallization. Hazy. |
| 7 days (seeding): | Stable. No crystallization. | Stable. No crystallization. | Stable. No crystallization. | Stable. No crystallization. Hazy. |

Manufacturing Method 1

Step 1: Weigh 60% of the SOLVESSO 200 the LABS acid+TOXIMUL 8320+TERMUL 1284 into a 250 ml beaker (vessel 1).

Step 2: Add a magnetic flea to the beaker, place beaker on a stirrer, commence stirring & add amine slowly (exothermic).

Step 3: Continue stirring at 40° C. for 30 min or until a homogenous mixture is obtained.

Step 4: While continuing to mix, add the water slowly.

Step 5: Weigh the MCPA acid & the Hallcomid 8-10 & 40% of SOLVESSO 200 into a 1 L beaker (vessel 2).

Step 6: Place beaker on a hot plate, commence stirring with an overhead mixer & heat to 65° C.

Step 7: Continue heating at 65° C. while stirring for ~30 min or until a homogenous mixture is obtained. Cool the contents of vessel 2 to 50° C.

Step 8: While stirring vessel 2 (at 50° C.), add contents of vessel 1 slowly to vessel 2. Commence cooling.

Step 9: Continue stirring for ~10 min and cool the mixture to 20° C.

Step 10: Filter the formulation through 100 micron GAF filter.

Manufacturing Method 2

Step 1: Weigh 60% of the SOLVESSO 200 the LABS acid+TOXIMUL 8320+TERMUL 1284 into a 250 ml beaker (vessel 1).

Step 2: Add a magnetic flea to the beaker, place beaker on a stirrer, commence stirring & add amine slowly (exothermic).

Step 3: Continue stirring at 40° C. for 30 min or until a homogenous mixture is obtained.

Step 4: While continuing to mix, add the water slowly.

Step 5: Weigh the MCPA acid & the Hallcomid 8-10 & 40% of SOLVESSO 200 into a 1 L beaker (vessel 2).

Step 6: Place beaker on a hot plate, commence stirring with an overhead mixer & heat to 65° C.

Step 7: Continue heating at 65° C. while stirring for ~30 min or until a homogenous mixture is obtained. Cool the contents of vessel 2 to 50° C.

Step 8: While stirring vessel 2 (at 50° C.), add contents of vessel 1 slowly to vessel 2. Commence cooling.

Step 9: Continue stirring for ~10 min and cool the mixture to 20° C.

Step 10: Filter the formulation through 100 micron GAF filter.

Example 21 and 22—EC Compositions of 2,4-D Plus Glyphosate

Compositions of acid herbicide emulsifiable concentrate containing both 2,4-D and glyphosate in acid form were prepared by combining the components in Table 13 in the parts by weight shown and using the manufacturing method described and were found to be stable.

TABLE 13

Glyphosate vehicle

| All g/L | A | F | F1 |
|---|---|---|---|
| Glyphosate as 100% | 262 | 240 | 240 |
| Propylene Glycol | 900 | 640 | 484 |
| MOPA 100% | 200 | 120 | 276 |

| | E21 | E22 |
|---|---|---|
| Glyphosate | 125 | 100 |
| 24D | 200 | 200 |
| Propylene Glycol | 125 | 260 |
| MOPA | 10 | 10 |

TABLE 13-continued

| | | |
|---|---|---|
| HOPA 100% Tomamine | | 50 |
| Hallcomid M8-10 | 225 | 300 |
| Solvesso 200 | 25 | 50 |
| Termul 1284 | 30 | 60 |
| Toximul 8320 | 25 | 50 |
| Kermat HF60 | | |
| emulsification D | Pass | Pass |
| emulsification C | Pass | Pass |
| 1% pH | 4.19 | 3.55 |
| Viscosity 5° C. cp | 72 | 469 |
| Viscosity 20° C. cp | 38 | 148 |
| Assay glyphosate g/L | | |
| Assay 24D g/L | | |

Manufacturing Method—

Weigh out Propylene Glycol n a 400 mL glass beaker and heat to 75° C. whilst stirring with an overhead stirrer.

1. Maintaining the temperature at 75° C. add in Glyphosate and stir vigorously until fully dispersed.
2. Whilst stirring add in MOPA (HOPA in E22) until a clear solution results. Add more MOPA if required to dissolve Glyphosate. Record amount and pH. This is the Glyphosate vehicle.
3. In a 2 L tall glass beaker add in Hallcomid M-8-10 and heat to 75° C. whilst stirring with an overhead stirrer.
4. Maintaining the temperature at 75° C. add in 24D and stir vigorously until fully dissolved.
5. In a 250 ml beaker add in Solvesso 200 followed by Toximul 8320 and Termul 1284 and heat to 50° C. and mix until a clear solution results.
6. While stirring vigorously and maintaining the temperature at 75° C. add in the above Solvesso 200 mix to the 24D solution and stir until homogenous and clear.
7. To the clear 24D emulsifier solution add the Glyphosate vehicle solution and mix and allow to cool.
8. Allow to return to RT and make to 1 L with Hallcomid.

Examples 23-27—EC Compositions of 2,4-D and Fluroxypyr

Emulsifiable concentrate compositions containing both 2,4-D acid and fluroxypyr acid were prepared using the components in the parts by weight shown in Table 14 and using the manufacturing method listed. The emulsifiable concentrates were found to have good stability.

TABLE 14

| | E23 (g) | E24 (g) | E25 (g) | E26 (g) | E27 (g) |
|---|---|---|---|---|---|
| Fluroxypyr | 110 | 110 | 110 | 110 | 110 |
| 24D | 200 | 200 | 200 | 200 | 200 |
| NMP | 50 | 50 | 50 | 50 | 50 |
| MOPA 100% | 10 | 20 | 30 | 50 | 20 |
| HOPA 100% | | | | | 10 |
| Hallcomid M8-10 | 480 | 480 | 480 | 480 | 480 |
| Solvesso 200 | 50 | 50 | 50 | 50 | 50 |
| Termul 1284 | 60 | 60 | 60 | 60 | 60 |
| Toximul 8320 | 50 | 50 | 50 | 50 | 50 |
| Appearance | Clear solution | Clear solution | Clear solution | Clear solution | Clear solution |
| Low temp stability | | | | | |
| 1% pH | 3.32 | 3.55 | 3.7 | 4.06 | 3.76 |
| Density | 1.067 | 1.067 | 1.067 | 1.066 | 1.067 |
| Emulsion A 30 min | 0.1 ml pass | 0 ml pass | 0 ml pass | 0 ml pass | 0 ml pass |
| Emulsion D 30 min | 0.1 ml pass | 0 ml pass | 0 ml pass | 0 ml pass | 0 ml pass |
| Emulsion A 2 hours | 0.2 ml pass | 0 ml pass | 0 ml pass | 0 ml pass | 0 ml pass |
| Emulsion D 2 hours | 0.2 ml pass | 0 ml pass | 0 ml pass | 0 ml pass | 0 ml pass |
| Foaming ml | 25 | 25 | 30 | 25 | |

Manufacturing Method—1 L batches with Fluroxypyr and 24D

1. Weigh out Hallcomid M-8-10 and NMP into a 2 L glass beaker and add in Fluroxypyr and heat on a hot plate to 75° C. whilst stirring with an overhead stirrer until a clear solution results.
2. When the above solution is clear add 2,4D and maintain at 75° C. whilst stirring with an overhead stirrer until a clear solution results.
3. To a 400 ml glass beaker with a magnetic stirrer add in Solvesso 200, Toximul 1284, and Toximul 8320 and mix at 50 C until homogenous and a clear solution results.
4. To the 2 L beaker add in the contents of the 400 ml beaker whilst vigorously stirring and maintain the temperature at 75° C.
5. Mix until homogenous and clear and allow to cool.
6. When at 40° C. check pH of 1% aqueous solution.
7. Add in Base and mix for ten minutes.
8. Allow to cool to 20° C. and fill into a 1 L batch and make up to volume with Hallcomid M-8-10.

Examples 28-35—Mixtures of 2,4-D and Picloram

Emulsifiable concentrate compositions containing both 2,4-D and picloram in acid form were prepared by combining the components in the parts by weight shown in Table 15 and using the manufacturing method described.

TABLE 15

| | Picloram/24D 22.5/360 g/L | | | | | | | |
|---|---|---|---|---|---|---|---|---|
| All g/L | E28 | E29 | E30 | E31 | E32 | E33 | E34 | E35 |
| Picloram as 100% | 22.5 | 22.5 | 22.5 | 22.5 | 22.5 | 64 | 64 | 64 |
| 2,4D as 100% | 360 | 360 | 360 | 360 | 360 | 240 | 240 | 240 |
| Hallcomid M8-10 | 520 | 520 | 510 | 510 | 510 | 550 | 550 | 550 |
| Solvesso 200 | 50 | 50 | 50 | 50 | 50 | 50 | 50 | 50 |
| Termul 1284 | 60 | 60 | | | | 60 | 60 | 60 |
| Toximul 8320 | 50 | 50 | 110 | 110 | 110 | 50 | 50 | 50 |
| MOPA 100% | 20 | 40 | 10 | 20 | 20 | 10 | 30 | 50 |
| Appearance | clear sol | clear sol | clear sol | clear sol | clear sol | clear sol | clear sol | clear sol |
| Low temp stability | clear sol | clear sol | clear sol | clear sol | clear sol | clear sol | clear sol | clear sol |
| 1% pH | 3.32 | 3.73 | 3.21 | 3.67 | 3.97 | 3.15 | 3.56 | 3.75 |
| Density | 1.073 | 1.073 | 1.074 | 1.074 | 1.074 | 1.049 | 1.049 | 1.049 |
| picloram g/L initial | 23.5 | 22.9 | 25.6 | 25.1 | 24.9 | 64.7 | 63.6 | 62.3 |
| picloram g/L initial HYD | 23.4 | | 25 | 24.6 | 23.8 | 64.1 | 63.3 | 62.8 |
| 24D g/L initial | 351 | | 357 | 350 | 346 | 242 | 238 | 233 |
| Emulsion A | pass | pass | pass | pass | pass | pass | pass | pass |
| Emulsion D | pass | pass | pass | pass | pass | pass | pass | pass |
| Foaming ml | 12 | 12 | 8 | 8 | 8 | 20 | | |

Manufacturing Method—1 L batches
1. Weigh out Hallcomid M-8-10 into a 2 L glass beaker and add in Picloram and heat on a hot plate to 75° C. whilst stirring with an overhead stirrer until a clear solution results.
2. When the above solution is clear add 2,4D and maintain at 75° C. whilst stirring with an overhead stirrer until a clear solution results.
3. To a 400 ml glass beaker with a magnetic stirrer add in Solvesso 200, Toximul 1284, and Toximul 8320 and mix at 50° C. until homogenous and a clear solution results.
4. To the 2 L beaker add in the contents of the 400 ml beaker whilst vigorously stirring and maintain the temperature at 75° C.
5. Mix until homogenous and clear and allow to cool.
6. When at 40° C. check 1% pH.
7. Add in Base and mix for ten minutes.
8. Allow to cool to 20° C. and fill into a 1 L batch and make up to volume with Hallcomid M-8-10.

Example 36—Comparison of the Influence of Small Amounts of Water on Stability of the Acid Form of Phenoxy Alkanoic Acids In the absence of water it was generally found that compositions of the invention undergo a small but nonetheless significant reduction in the alkanoic acid herbicide content with ageing as a result of the formation of esters and/or amides as shown in Schemes 1 and 2. While these products formed are herbicidal it is desirable to maintain a highly stable content of the active in the alkanoic acid form.

When the 2,4-D compositions of the invention, in the absence of water, were subject to accelerated aging (2 weeks at 54° C.) the content of the 2,4-D herbicide in the acid form compared with the total 2,4-D herbicide in all forms (including acid and ester/amide forms) was determined for a number of compositions.

The loss of 2,4-D in acid form as a result of transformation during accelerated aging was found to be as follows:

| | |
|---|---|
| Average % 2,4-D loss = | 10.1% |
| Average g/kg loss = | 41.2 g/Kg |
| Maximum % 2,4-D loss = | 15.2% |
| Maximum g/kg = | 61.0 g/Kg |
| Minimum % 2,4-D loss = | 4.3% |
| Minimum g/Kg loss = | 17.2 g/Kg |

The presence of about 2% w/w of water in the identified compositions of the invention identified as containing water provided a significant improvement in the retention and long term stability of the 2,4-D herbicide in acid form.

Composition of the invention comprising about 2% added water were found to undergo an average loss of 2,4-D in acid form with accelerated aging (2 weeks at 54° C.) as follows:

| | |
|---|---|
| Average % 2,4-D loss = | 1.5% |
| Average g/kg loss = | 6.0 g/Kg |
| Maximum % 2,4-D loss = | 2.2% |
| Maximum g/kg = | 9.0 g/Kg |
| Minimum % 2,4-D loss = | 0.51% |
| Minimum g/Kg loss = | 2 g/Kg |

Typical losses of MCPA compositions of the invention in the absence of water addition, when measured via free acid assay, were found to be in the same range as those determined for 2,4-D in the absence of water, as summarised above. The stability of the MCPA compositions of the invention with addition of water were found to follw the above reported trends seen in 2,4-D formulations.

Method—Summary, Free Phenoxy-alkonic Acid Content Analysis:

Acid content and the change in acid content with time was determined for compositions using the following procedure for determine free acid content and total phenoxyalkanoic acid content including acid transformed through ester and/or amide formation.

Samples of the formulations are diluted in a solution of acetonitrile and water (70:30), with internal standard added. The free phenoxy-alkonic acid content of the formulations are determined by HPLC using a C18 column, gradient elution and UV detection. Quantitation is carried out via internal standard calibration. The method is specific only for phenoxyalkonic acids in their free acid form any other species of the phenoxyalkonics are not detected nor are they converted back to their acid form via this analysis.

Method Summary Total Phenoxy-alkonic acid Content Analysis:

Samples of the formulations are dispersed in a solution of sodium hydroxide, with internal standard added. The solutions are then heated at 70° C. for 15 mins, to covert all transformation products to their acid form. The total phenoxy-alkonic acid content in the formulations is determined by HPLC using a C18 column, gradient elution and UV detection. Quantitation is carried out via internal standard calibration.

The method has been validated and therefore proven to recover/convert all phenoxyalkonic species back to their original input acid form.

Example 37

The following composition of Table 16 was prepared by combining the components in the amounts listed using the manufacturing method described. The composition had properties shown in Table 17.

TABLE 16

| (40% 2,4-D acid EC) - Using Hallcomid M-12-14. | | |
| --- | --- | --- |
| 40% w/w 2,4-D acid EC. | 2,4-D acid 98% | 408.0 g |
| | LABS acid | 40.0 g |
| | TOXIMUL 8320 | 70.0 g |
| | Triethylamine (TEA) | 50.0 g |
| | SOLVESSO 200 | 100.0 g |
| | Hallcomid M-12-14 | 332.0 g |

Manufacturing Method
Step 1: Weigh 60% of the SOLVESSO 200 the LABS acid, TOXIMUL 8320 into a 1 L beaker (V 1).
Step 2: Commence stirring with an over head stirrer & add the triethylamine slowly (exothermic).
Step 3: Continue stirring for ~30 min or until a homogenous mixture is obtained.
Step 4: Weigh the 2,4-D acid & the Hallcomid M-12-14 & 40% of SOLVESSO 200 into a 2 L beaker (V2).
Step 5: Place beaker on a hot plate, commence stirring with an overhead mixer & heat to 70° C.
Step 6: Continue heating at 70° C. while stirring for ~30 min or until a homogenous mixture is obtained.
Step 7: Cool the contents of V2 to 50° C.
Step 8: While stirring V2 (at 50° C.), add contents of V1 slowly to V2.
Step 9: Mix the contents of V2 for a further 10 min.
Step 10: Continue stirring for a further ~20 min while cooling the mixture to 20° C.
Step 11: Filter the formulation through 100 micron GAF filter.

TABLE 17

| Parameters | INITIAL | 2 w at 54° C. |
| --- | --- | --- |
| Appearance | Yellow clear liquid | Yellow clear liquid |
| Active content (2,4-D), g/kg | 398 (436 g/L) | 395 (433 g/L) |
| Density (20° C.), g/ml | 1.096 | 1.096 |
| Viscosity (cP) Spindle: S21 Speed: 12 RPM Temp.: 20° C. | 225.4 | 227.3 |
| Viscosity (cP) Spindle: S21 Speed: 3 RPM Temp.: 5° C. | 862.5 | 859.2 |
| Persistent Foam test (CIPAC MT47.2) (5% dilution in CIPAC STD C water) | 20 ml | 20 ml |
| pH (1% dilution in DI water) | 3.34 | 3.29 |
| Emulsion Stability (CIPAC MT36.1) CIPAC STD A water | Good emulsification. | Good emulsification. |
| % Oil (30 min; 2 h; 4 hrs) | (0; 0; 0) | (0; 0; 0) |
| % cream (30 min; 2 h; 4 hrs) | (0.2; 0.5; 0.8) | (0.2; 0.5; 0.8) |
| Low temp storage stab. (CIPAC MT39.3) | | |
| 24 hrs: | | Stable. No crystallization. |
| 7 days (seeding): | | Stable. No crystallization. |

Example 38

The following composition of Table 18 was prepared by combining the components in the amounts listed using the manufacturing method described. The composition had properties shown in Table 19.

TABLE 18

| (40% 2,4-D acid EC) - Using Hallcomid 1025. | | |
| --- | --- | --- |
| 40% w/w 2,4-D acid EC. | 2,4-D acid 98% | 408.0 g |
| | LABS acid | 40.0 g |
| | TOXIMUL 8320 | 70.0 g |
| | Triethylamine (TEA) | 50.0 g |
| | SOLVESSO 200 | 100.0 g |
| | Hallcomid 1025 | 332.0 g |

Manufacturing Method
Step 1: Weigh 60% of the SOLVESSO 200 the LABS acid, TOXIMUL 8320 into a 1 L beaker (V 1).
Step 2: Commence stirring with an over head stirrer & add the triethylamine slowly (exothermic).
Step 3: Continue stirring for ~30 min or until a homogenous mixture is obtained.
Step 4: Weigh the 2,4-D acid & the Hallcomid 1025 & 40% of SOLVESSO 200 into a 2 L beaker (V2).
Step 5: Place beaker on a hot plate, commence stirring with an overhead mixer & heat to 70° C.
Step 6: Continue heating at 70° C. while stirring for ~30 min or until a homogenous mixture is obtained.
Step 7: Cool the contents of V2 to 50° C.
Step 8: While stirring V2 (at 50° C.), add contents of V1 slowly to V2.
Step 9: Mix the contents of V2 for a further 10 min.
Step 10: Continue stirring for a further ~20 min while cooling the mixture to 20° C.
Step 11: Filter the formulation through 100 micron GAF filter.

TABLE 19

| Parameters | INITIAL | 2 w at 54° C. |
| --- | --- | --- |
| Appearance | Yellow clear liquid | Yellow clear liquid |
| Active content (2,4-D), g/kg | 403 (447 g/L) | 399 (443 g/L) |
| Density (20° C.), g/ml | 1.109 | 1.109 |

TABLE 19-continued

| Parameters | INITIAL | 2 w at 54° C. |
|---|---|---|
| Viscosity (cP) Spindle: S21 Speed: 12 RPM Temp.: 20° C. | 163.7 | 164.5 |
| Viscosity (cP) Spindle: S21 Speed: 6 RPM Temp.: 5° C. | 530.5 | 531.8 |
| Persistent Foam test (CIPAC MT47.2) (5% dilution in CIPAC STD C water) | 20 ml | 20 ml |
| pH (1% dilution in DI water) | 3.28 | 3.25 |
| Emulsion Stability (CIPAC MT36.1) CIPAC STD A water | Good emulsification. | Good emulsification. |
| % Oil (30 min; 2 h; 4 hrs) | (0; 0; 0) | (0; 0; 0) |
| % cream (30 min; 2 h; 4 hrs) CIPAC STD D water | (1.5; 2; 4) | (1; 1.5; 2) |
| % Oil (30 min; 2 h; 4 hrs) | (0; 0; 0) | (0; 0; 0) |
| % cream (30 min; 2 h; 4 hrs) Low temp storage stab. (CIPAC MT39.3) | (1.8; 3; 4) | (1; 1.5; 2) |
| 24 hrs: | | Stable. No crystallization. |
| 7 days (seeding): | | Stable. No crystallization. |

In the Examples, the Products Identified are as Follows:
Atlas™ G-5002 L—butyl block copolymer polymeric nonionic oil-in-water emulsifier.
Synperonic™ A11—polyoxyethylene (11) $C_{12}$-$C_{15}$ alcohol non-ionic emulsifier.
Calsogen™ ARL 100ND—alkyl benzene sulfonate anionic emulsifier.
Solvesso™ 200—alkylbenzene IBP 220° C.
Tomamine™—PA—10 L is a commercial brand of hexyloxypropylamine available from Air Products and Chemicals, Inc.
KEMMAT™ HF60—calcium dodecyl benzene sulfonate.
TERMUL™ 1284—ethoxylated castor oil emulsifier.
TOXIMUL™ 8320—butyl block copolymer, polymeric emulsifier.
HALLCOMID™ M 8-10 N,N-dimethyl decanamide
HALLCOMID™ M-12-14—mixture of N,N-dimethyllauricamide and N,N-dimethylmyristicamide
HALLCOMID™ 1025-N,N-dimethyl 9-decanamide
MEA—monoethanolamine
TIPA—triisopropanolamine
MIPA—monoisopropylamine
DEA—diethanolamine
TEA—triethanolamine
EDA—ethylenediamine
DETA—diethylenetriamine
MOPA—methoxypropylamine
HOPA—hexyloxypropylamine
Rhodiasolv™ Match 111—non-ionic solvent blend
BEROL™ 106—ethoxylated castor oil

The invention claimed is:

1. A stable emulsifiable concentrate of a phenoxy-alkanoic acid herbicide comprising a phenoxy-alkanoic acid herbicide in the form of the free acid dissolved in an amide solvent and at least one amine wherein:

A. the amine is of formula (I)

wherein:
$R^1$, $R^2$ and $R^3$ are $C_1$ to $C_{10}$ alkyl; or
$R^1$, $R^2$ and $R^3$ are independently selected from the group consisting of hydrogen, $C_1$ to $C_{10}$ alkyl and $C_1$ to $C_{10}$ alkyl substituted with a substituent selected from the group consisting of hydroxyl, $C_1$ to $C_{10}$ alkoxy, amino, $C_1$ to $C_6$ alkylamino and di-($C_1$ to $C_6$ alkyl)amino and wherein at least one of $R^1$, $R^2$ and $R^3$ is other than hydrogen and $C_1$ to $C_{10}$ alkyl; or
two of $R^1$, $R^2$ and $R^3$ together form a ring of 5 or 6 constituent ring members selected from the group consisting of methylene, —O—, —N— and N($C_1$ to $C_6$-alkyl)- and the other of $R^1$, $R^2$ and $R^3$ is selected from hydrogen, $C_1$ to $C_6$ alkyl and $C_1$ to $C_6$ alkyl substituted with a substituent selected from the group consisting of hydroxyl, $C_1$ to $C_6$ alkoxy, amino and $C_1$ to $C_6$ alkylamino; and B. the amide solvent comprises at least one compound of formula (II):

wherein
$R^4$ is selected from the group consisting of hydrogen and $C_1$ to $C_{17}$ hydrocarbyl;
$R^5$ is selected from the group consisting of $C_1$ to $C_{15}$ hydrocarbyl;
$R^6$ is selected from the group consisting of $C_1$ to $C_{15}$ hydrocarbyl; and
$R^5$ and $R^6$ may together form a ring incorporating the nitrogen of the amide comprising 4 or 5 methylene groups wherein the concentrate is clear and has no crystallization.

2. An emulsifiable concentrate according to claim 1, wherein
in the amine of formula (I) $R^1$, $R^2$ and $R^3$ are independently selected from the group consisting of hydrogen, $C_1$ to $C_{10}$ alkyl; $C_1$ to $C_{10}$ alkyl substituted with a substituent selected from the group consisting of hydroxyl, $C_1$ to $C_{10}$ alkoxy, amino, $C_1$ to $C_6$ alkylamino and di-($C_1$ to $C_6$ alkyl)amino; and wherein at least one of $R^1$, $R^2$ and $R^3$ is other than hydrogen and $C_1$ to $C_{10}$ alkyl.

3. An emulsifiable concentrate according to claim 1, wherein the amine comprises at least one amine of formula (I),
wherein either (i) $R^1$, $R^2$ and $R^3$ are $C_1$ to $C_4$ alkyl; (ii) $R^1$, $R^2$ and $R^3$ are $C_2$ to $C_4$ alkanol; or (iii) $R^1$ is $C_1$ to $C_{10}$ alkoxy substituted $C_2$ to $C_4$ alkyl and $R^2$ and $R^3$ are independently hydrogen or $C_1$ to $C_4$ alkyl.

4. An emulsifiable concentrate according to claim 1, wherein the amine comprises at least one of formula (I) wherein (i) $R^1$, $R^2$, and $R^3$ are $C_1$ to $C_4$ alkyl; (ii) $R^1$, $R^2$ and $R^3$ are independently selected from $C_2$ to $C_4$ alkanol or (iii) $R^1$ is selected from $C_1$ to $C_6$ alkoxy-substituted alkyl and $R^2$ and $R^3$ are hydrogen or $C_1$ to $C_4$ alkyl.

5. An emulsifiable concentrate according to claim 1, wherein the amine is selected from the group consisting of triethanolamine, triisopropanolamine, methoxypropylamine, hexyloxypropylamine and mixtures of two or more thereof.

6. An emulsifiable concentrate according to claim 1, wherein the amine is present in an amount of from 0.5% to 5% by weight of the amine based on the weight of emulsifiable concentrate.

7. An emulsifiable concentrate according to claim 1, wherein in the amide solvent of formula (II)
$R^5$ and $R^6$ are independently selected from the group consisting of $C_1$ to $C_6$ hydrocarbyl and the group wherein $R^5$ and $R^6$ together form a ring incorporating the nitrogen of the amine by a bridging group $R^5 \ldots R^6$ of formula —$CH_2 CH_2 CH_2 CH_2$— or —$CH_2 CH_2 CH_2 CH_2 CH_2$—.

8. An emulsifiable concentrate according to claim 1, wherein in the amide solvent of formula (II)
$R^4$ is $C_6$ to $C_{17}$ alkyl; and
$R^5$ and $R^6$ are independently selected from $C_1$ to $C_4$ alkyl.

9. An emulsifiable concentrate according to claim 1, wherein amide solvent is selected from the group consisting of N,N-dimethyl octanamide, N,N-dimethyl decanamide, N,N-dimethyl caprylamide, N,N-dimethyl 2-ethylhexanoamide, N,N-dimethyl oleamide, N,N-dimethyllauricamide, N,N-dimethylmyristicamide, N,N-dimethyl 9-decenamide and mixtures of two or more thereof.

10. An emulsifiable concentrate according to claim 1, wherein the amide solvent is present in an amount of from 25% to 60% by weight of the amide solvent based on the weight of the emulsifiable concentrate composition.

11. An emulsifiable concentrate according to claim 1, wherein phenoxy-alkanoic acid herbicide comprises at least one selected from the group consisting of:
phenoxyacetic herbicides selected from 2,4-D and MCPA;
phenoxybutyric herbicides selected from the group consisting of 4-CPB, 2,4-DB, 3,4-DB, MCPB and 2,4,5-TB; and
phenoxypropionic herbicides selected from the group consisting of dichlorprop, dichlorprop-P, fenoprop, mecoprop and mecoprop-P.

12. An emulsifiable concentrate according to claim 1, wherein the phenoxy-alkanoic acid herbicide is 2,4-D, MCPA or a mixture thereof.

13. An emulsifiable concentrate according to claim 1, wherein phenoxy-alkanoic acid herbicide is present in a total amount of at least 200 g acid per liter of emulsifiable concentrate.

14. An emulsifiable concentrate according to claim 1, wherein the phenoxy-alkanoic acid is present in a total amount of at least 400 g acid per liter of emulsifiable concentrate.

15. An emulsifiable concentrate according to claim 1, further comprising a hydrocarbon co-solvent which has a flash point of at least 60.5° C. and comprises at least one hydrocarbon selected from alkyl substituted aromatics.

16. An emulsifiable concentrate according to claim 15, wherein the hydrocarbon co-solvent is present in an amount in the range of from 2% to 25% w/w of the emulsifiable concentrate.

17. An emulsifiable concentrate according to claim 1, comprising emulsifier in an amount in the range of from 5% w/w to 25% w/w of the emulsifiable concentrate composition which comprises a non-ionic emulsifier selected from alcohol ethoxylates, fatty acid ethoxylates, fatty amide ethoxylates and EO/PO block copolymers including butyl based block copolymers, in an amount in the range of from 2% w/w to 20% w/w of the emulsifiable concentrate composition.

18. An emulsifiable concentrate according to claim 1 comprising emulsifier in an amount in the range of from 5% w/w to 25% w/w of the emulsifiable concentrate composition which comprises anionic emulsifier in an amount of from 1% to 10% w/w of the composition and non-ionic emulsifier in an amount of from 2% to 15% w/w of the composition.

19. An emulsifiable concentrate according to claim 1 comprising no more than 5% water based on the weight of the emulsifiable concentrate.

20. A method of controlling weeds comprising providing a phenoxy-alkanoic acid emulsifiable concentrate according to claim 1, diluting the concentrate with water to provide an emulsion and applying the diluted concentrate to the weeds to be controlled.

21. An emulsifiable concentrate according to claim 1, wherein the amine of formula (I) is triethylamine.

* * * * *